United States Patent [19]

Matsuo et al.

[11] 4,416,817
[45] Nov. 22, 1983

[54] 3-METHOXY-2-OXOAZETIDINE DERIVATIVES AND THEIR PRODUCTION

[75] Inventors: Taisuke Matsuo, Ibaraki; Michihiko Ochiai, Osaka, both of Japan

[73] Assignee: Takeda Chemical Industries, Ltd., Osaka, Japan

[21] Appl. No.: 322,661

[22] Filed: Nov. 18, 1981

Related U.S. Application Data

[63] Continuation of Ser. No. 152,808, May 23, 1980, abandoned.

[30] Foreign Application Priority Data

Jun. 8, 1979 [JP] Japan .................................. 54-72812
Mar. 22, 1980 [JP] Japan .................................. 55-36365

[51] Int. Cl.³ ................... C07D 205/08; C07D 403/14; C07D 403/12; C07D 403/06
[52] U.S. Cl. ............................ 260/239 A; 544/316; 544/317; 260/245.4; 544/320; 544/321; 260/330.3; 544/323; 544/324; 260/330.9; 544/325; 544/327; 544/111; 544/328; 544/329; 544/112; 544/331; 544/332; 544/113; 544/333; 544/334; 544/114; 544/335; 544/359; 544/120; 544/360; 544/362; 544/121; 544/363; 544/364; 544/122; 544/365; 544/366; 544/123; 544/367; 544/369; 544/132; 544/370; 544/372; 544/133; 546/122; 546/123; 544/134; 546/155; 546/156; 544/137; 546/157; 546/159; 544/138; 546/168; 546/170; 544/139; 546/171; 546/172; 544/141; 546/175; 546/114; 544/146; 546/275; 546/276; 544/152; 546/277; 546/280; 544/182; 546/281; 546/283; 544/209; 546/284; 546/153; 544/212; 544/238; 544/279; 544/295; 544/296; 544/300; 544/301; 544/310; 544/311; 544/312

[58] Field of Search ............. 260/239 A, 245.4, 330.3, 260/330.9; 544/111, 112, 113, 114, 120, 121, 122, 123, 133, 134, 137, 138, 132, 139, 141, 146, 152, 182, 209, 212, 238, 279, 295, 296, 300, 301, 310, 311, 312, 316, 317, 320, 321, 323, 324, 325, 327, 328, 329, 331, 332, 333, 334, 335, 360, 362, 363, 364, 365, 366, 367, 369, 370, 372; 546/112, 122, 123, 153, 155, 156, 157, 159, 168, 170, 171, 172, 175, 275, 276, 277, 280, 281, 283, 284

[56] References Cited

FOREIGN PATENT DOCUMENTS 1519495 7/1978 United Kingdom .

OTHER PUBLICATIONS

Durbin et al., Phytochemistry 17, 147, (1978).
Zervas et al., J. Amer. Chem. Soc. 87, 99, (1965).

Primary Examiner—Mark L. Berch
Attorney, Agent, or Firm—Wenderoth, Lind & Ponack

[57] ABSTRACT

Novel 3-methoxy-2-oxoazetidine derivatives, which are shown by the following formula

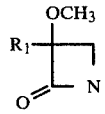

wherein $R_1$ is amino, acylated amino or protected amino, are of value as intermediates for the synthesis of useful compounds represented by the formula

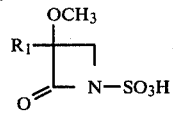

wherein $R_1$ has the same meaning as defined above, as drugs in the treatment of bacterial infections.

12 Claims, No Drawings

3-METHOXY-2-OXOAZETIDINE DERIVATIVES AND THEIR PRODUCTION

This application is a continuation of application Ser. No. 152,808, filed May 23, 1980 (now abandoned).

The present invention provides novel 3-methoxy-2-oxoazetidine derivatives of the formula (I)

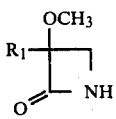  (I)

wherein $R_1$ is amino, acylated amino or protected amino, which are of value as intermediates for the synthesis of useful medicines.

The object compounds of the formula (I) may be produced by oxidizing 3-methoxy-2-oxoazetidine-1-(α-isopropylidene)acetic acid ester derivative of the formula (VI):

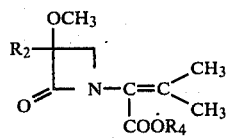  (VI)

wherein $R_2$ is acylated amino or protected amino; $R_4$ is an ester residue, and optionally removing the amino-projecting group; and the a object compounds of the fomrula (II):

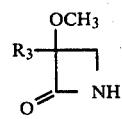  (II)

wherein $R_3$ is acylated amino, may also be produced by acylating 3-amino-3-methoxy-2-oxoazetidine.

Referring to the above general formulas, the acyl groups on the acylated amino groups $R_1$, $R_2$ and $R_3$ may, for example, be the acyl groups which are found as substituents on the 6-amino group of the known penicillin derivatives and the 7-amino group of the known cephalosporin derivatives.

Among specific examples of such acyl groups are the following:

groups of the formula $R_6$—CO— [wherein $R_6$ is a lower alkyl group or a substituted or unsubstituted heterocyclic group];

groups of the formula:

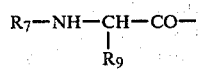

{wherein $R_7$ is hydrogen, optionally substituted amino acid residue, amino-protecting group, a group of the formula $R_8$—$(CH_2)_n$—CO— [$R_8$ is optionally substituted heterocyclic group, optionally substituted phenyl, optionally substituted lower alkyl, optionally substituted phenylthio or lower alkylthio; n is an integer of 0 to 4, the group —$(CH_2)_n$—may optionally be substituted], a group of the formula

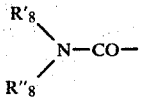

[$R'_8$ and $R''_8$ may be same or different, and are hydrogen, lower alkyl, lower alkyl carbamoyl, optionally substituted phenylcarbonyl or sulfo] or a group of the formula $R'''_8$—$SO_2$—[$R'''_8$ is optionally substituted lower alkyl]; $R_9$ is hydrogen, optionally substituted lower alkyl, optionally substituted phenyl, optionally substituted heterocyclic group, cycloalkenylene or optionally substituted heterocyclecarbonylamino in which an alkylene chain may stand between the heterocyclic and carbonylamino moieties.};

groups of the formula:

{wherein $R_{10}$ is a group of the formula

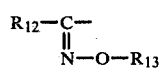

[$R_{12}$ is optionally substituted heterocyclic group or optionally substituted phenyl, $R_{13}$ is hydrogen, optionally substituted lower acyl, lower alkyl or a group of the formula —$R_{14}$—$R_{15}$($R_{14}$ is lower alkylene or lower alkylene; $R_{15}$ is carboxyl, ester thereof or heterocyclic group)]; $R_{11}$ is a chemical bond or a group of the formula

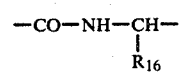

($R_{16}$ is a lower alkyl, optionally substituted phenyl or optionally substituted heterocyclic group)};

groups of the formula:

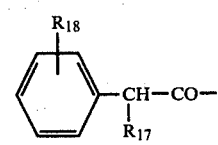

[wherein $R_{17}$ is hydroxy, sulfoxy, carboxyl, optionally substituted sulfamoyl, sulfo, optionally substituted phenoxycarbonyl, benzyloxycarbonyl or formyloxy; $R_{18}$ is hydrogen, a lower alkyl group, a lower alkoxy group, halogen, nitro or hydroxy]; and groups of the formula:

[wherein $R_{19}$ is a cyano, optionally substituted phenyl, optionally substituted phenoxy, optionally substituted lower alkyl, optionally substituted alkenyl or optionally substituted heterocyclic group; $R_{20}$ is a chemical bond or —S—].

The lower alkyl group $R_6$ is preferably a group of 1 to 6 carbon atoms. The heterocyclic moiety of optionally substituted heterocyclic group $R_6$ is a 5- to 6-membered heterocyclic group including 1 to 2 nitrogen atoms and may optionally include a single oxygen atom. Examples of said heterocyclic group include isoxazolyl, piperazinyl, imidazolinyl, etc. The substituents on such heterocyclic groups may, for example, be lower alkyl of 1 to 3 carbon atoms, lower alkoxy of 1 to 3 carbon atoms, halogen, nitro, amino, oxo, thioxo and optionally substituted phenyl. The substituents on the aforementioned optionally substituted phenyl group may include, for example, lower alkyl of 1 to 3 carbon atoms, lower alkoxy of 1 to 3 carbon atoms, halogen, nitro and amino.

As examples of the amino acid residue of the optionally substituted amino acid residue $R_7$, there may be mentioned glycyl, alanyl, valyl, leucyl, isoleucyl, seryl, threonyl, cysteinyl, cystyl, methionyl, $\alpha$- or $\beta$-aspartyl, $\alpha$- or $\gamma$-glutamykl, lysyl, arginyl, phenylalanyl, phenylglycyl, tyrosyl, histidyl, tryptophyl, prolyl, etc. The substituents on the aforementioned optionally substituted amino acid residues may include, for example, amino, lower alkyl amino, amino-protecting group, carbamoyl, methylcarbamoyl, sulfamoyl, benzyl, 4-ethyl-2,3-dioxo-1-piperadinocarbonyl and 4-ethyl-2,3-dioxo-1-piperidinocarbonylamino. The lower alkyl moiety of the lower alkyl amino is preferably alkyl of 1 to 3 carbon atoms. The amino-protecting group may, for example, be one of the protective groups mentioned hereinafter for amino group. The amino-protecting group $R_7$ may, for example, be one of the protective groups mentioned hereinafter for amino group.

The optionally substituted heterocyclic group $R_8$ in the group represented by the formula $R_8-(CH_2)_n-CO-$ includes, for example, 5- to 6-membered heterocyclic groups including one sulfur, nitrogen or oxygen atom, 5- to 6-membered heterocyclic groups including 2 to 4 nitrogen atoms, and 5- to 6-membered heterocyclic groups including one or two nitrogen atoms and one sulfur or oxygen atom. These heterocyclic groups may each be fused to a 6-membered ring including one or two nitrogen atoms, a benzene ring or a 5-membered ring including one sulfur atom. As examples of said heterocyclic group $R_8$, there may be mentioned 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthyridinyl, 1,5-naphthyridinyl, 1,6-naphthyridinyl, 1,7-naphthridinyl, 2,7-naphthyridinyl, 2,6-naphthyridinyl, quinolyol, thieno[2,3-b]pyridinyl, tetrazolyl, thiadiazolyl, oxadiazolyl, triazinyl, thienyl, pyrolyl, furyl, etc. The substitutents on such optionally substituted heterocyclic groups $R_8$ include, for example, optionally substituted alkyl of 1 to 12 carbon atoms, lower alkoxy of 1 to 3 carbon atoms, hydroxy, oxo, thioxo, formyl, trifluoromethyl, amino, halogen, lower alkylsulfonyl of 1 to 3 carbon atoms, coumarin-3-carbonyl, 4-formyl-1-piperazinyl, pyrrolaldoimino, furanaldoimino, thiophenaldoimino, mesyl, amino-protecting group, acylamino of 2 to 4 carbon atoms which may be substituted by halogen, etc. The amino-protecting group may, for example, be one of the protective groups mentioned hereinafter for amino group. The substituents on the optionally substituted alkyl of 1 to 12 carbon atoms include, for example, phenyl, halogen, hydroxy, dialkylamino, etc. The alkyl moiety of the dialkylamino is preferably alkyl of 1 to 3 carbon atoms.

The substituents on the optionally substituted phenyl group $R_8$ include, for example, lower alkyl of 1 to 3 carbon atoms, lower alkoxy of 1 to 3 carbon atoms, halogen, hydroxy and amino. The lower alkyl moiety of the lower alkylthio group $R_8$ is preferably alkyl of 1 to 3 carbon atoms.

The substituents on the optionally substituted phenylthio group $R_8$ include, for example, lower alkyl of 1 to 3 carbon atoms, lower alkoxy of 1 to 3 carbon atoms, halogen, hydroxy, amino, etc.

The substituents which may optionally be substituted on the group represented by the formula $-(CH_2)_n-$ include, for example, amino and the group of the formula $-NH-COR''''_8$ [$R''''_8$ is amino or optionally substituted piperazinyl]. As examples of the substituent on said optionally substituted piperazinyl group $R''''_8$, there may be mentioned lower alkyl of 1 to 3 carbon atoms, lower alkoxy of 1 to 3 carbon atoms, hydroxy, oxo, thioxo and halogen.

Referring to the above formula, the lower alkyl represented by $R'_8$ and/or $R''_8$ is preferably the group of 1 to 3 carbon atoms. The lower alkyl moiety of the lower alkyl-carbamoyl is preferably the group of 1 to 3 carbon atoms.

As examples of the substituents on said optionally substituted phenylcarbonyl group, there may be mentioned lower alkyl of 1 to 3 carbon atoms, lower alkoxy of 1 to 3 carbon atoms, halogen, hydroxy, sulfoxy, benzyloxy, etc.

The lower alkyl moiety of the optionally substituted lower alkyl group $R'''_8$ in the formula $R'''_8-SO_2-$ is preferably the moiety of 1 to 6 carbon atoms, which may be substituted by one or two substituents such as amino, carboxy, benzyloxycarbonyl or protected amino. The protective group in the protected amino may for example be one of the protective groups mentioned hereinafter for amino group.

The lower alkyl moiety of the optionally substituted lower alkyl group $R_9$ is preferably the moiety of 1 to 3 carbon atoms. As examples of the substituent on the optionally substituted lower alkyl, there may be mentioned phenyl, carbamoyl, methylcarbamoyl, methylthio, thienylacetamido, ethoxycarbonylmethylcarbamoyl, N-methyltetrazolylthio, halogen and sulfamoyl. The substituents on optionally substituted phenyl groups $R_9$ include, for example, lower alkyl of 1 to 3 carbon atoms, lower alkoxy of 1 to 3 carbon atoms, halogen, hydroxy, sulfoxy, benzyloxy, benzoyloxy, trimethylsilyl, acyloxy of 2 to 10 carbon atoms, etc. The heterocyclic ring on said optionally substituted heterocyclic group $R_9$ may, for example, be five-membered heterocyclic groups with one sulfur, nitrogen or oxygen atom, five-membered heterocyclic groups with one or two nitrogen atoms and one sulfur or oxygen atom and five- to six-membered heterocyclic groups with 2 to 4 nitrogen atoms. Examples of such heterocyclic groups are thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl, oxadiazolyl, etc. The substituents in these cases are lower alkyl of 1 to 3 carbon atoms, lower alkoxy of 1 to 3 carbon atoms, halogen, hydroxy, nitro, sulfoxy, amino and acylamino of 2 to 4 carbon atoms which may optionally be substituted by halogen etc.

The cycloalkenylene $R_9$ is preferably five- to six-membered cycloalkenylene, such as cyclohexenyl, cyclohexadienyl. The heterocyclic moiety of said optionally substituted heterocyclic carbonylamide which may optionally have an alkylene chain between the heterocyclic and carbonylamino group represented by $R_9$ includes, for example, six-membered heterocyclic group with two nitrogen atoms. Among such heterocyclic groups is piperazinyl. The substituents may for example be alkyl of 1 to 12 carbon atoms, lower alkoxy of 1 to 3 carbon atoms, oxo, thioxo, amino and so forth. The alkylene chain is preferably a alkylene chain of 1 to 3 carbon atoms and as examples of the chain there may be mentioned methylene, ethylene and n-propylene.

Referring, further, to the above formulas, the heterocyclic ring of said optionally substituted heterocyclic group $R_{12}$ in the group $R_{10}$ represented by the formula:

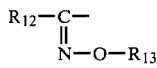

includes, for example, five-membered heterocyclic groups including one nitrogen, sulfur or oxygen atom, which five-membered heterocyclic groups may optionally include nitrogen atom or no nitrogen atom. Among examples of said heterocyclic group are 2-thiazolyl, 4-thiazolyl, 5-thiazolyl, 2-thienyl, 3-thienyl, 2-furyl, 3-furyl, 2-pyrrolyl, 3-pyrrolyl, etc. The substituents on such heterocyclic group include, for example, lower alkyl of 1 to 3 carbon atoms, lower alkoxy of 1 to 3 carbon atoms, hydroxy, halogen, amino, and acylamino group of 2 to 4 carbon atoms which may optionally be substituted by halogen.

The substituents on the optionally substituted phenyl group $R_{12}$ include, for example, lower alkyl of 1 to 3 carbon atoms, lower alkoxy of 1 to 3 carbon atoms, halogen, nitro, amino, hydroxy and substituted hydroxy.

The substituents of said substituted hydroxy may for example be benzyl, benzoyl, acyl of 2 to 10 carbon atoms, γ-D-glutamyl, 3-amino-3-carboxypropyl.

The lower alkyl group $R_{13}$ is preferably a group of 1 to 3 carbon atoms. The optionally substituted lower acyl group $R_{13}$ is preferably a group 2 to 4 carbon atoms and the substituents of said acyl group may for example be halogen. The lower alkylene $R_{14}$ in the group $-R_{14}-R_{15}$ of the group $R_{13}$ is preferably the group of 1 to 3 carbon atoms, such as methylene, ethylene, propylene, isopropylene, etc. The lower alkenylene $R_{14}$ is preferably the group of 1 to 3 carbon atoms, such as vinylene, propenylene, etc. The carboxyl ester $R_{15}$ may for example be the methyl ester, ethyl ester, propyl ester, etc. The heterocyclic group $R_{15}$ may, for example, be six-membered heterocyclic groups with one nitrogen and one oxygen atom, such as morpholino, etc.

The lower alkyl group $R_{16}$ in the group $R_{11}$ as represented by the formula:

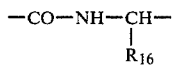

is preferably the group of 1 to 3 carbon atoms. As examples of substituents on optionally substituted phenyl groups $R_{16}$, there may be mentioned lower alkyl of 1 to 3 carbon atoms, lower alkoxy of 1 to 3 carbon atoms, halogen, nitro, amino, acyloxy of 2 to 10 carbon atoms, etc. The optionally substituted heterocyclic group $R_{16}$ may, for example, be five-membered heterocyclic groups with one sulfur, nitrogen or oxygen atoms, five-membered heterocyclic groups with one to two nitrogen atoms and one sulfur or oxygen atom and five-membered heterocyclic groups with two to four nitrogen atoms, such as thiazolyl, isothiazolyl, oxazolyl, isoxazolyl, thienyl, furyl, pyrrolyl, thiadiazolyl, oxadiaxolyl, triazinyl, tetrazolyl, imidazolyl, pyrazinyl, pyrimidinyl, pyridazinyl, piperazinyl, etc. The substituents on said optionally substituted heterocyclic group include, for example, lower alkyl of 1 to 3 carbon atoms, lower alkoxy of 1 to 3 carbon atoms, halogen, hydroxy, amino and acylamino group of 2 to 4 carbon atoms which may optionally be substituted by halogen.

Substituents on optionally substituted sulfamoyl groups $R_{17}$ include, for example, lower alkyl of 1 to 3 carbon atoms, amidino, etc. Substituents on optionally substituted phenoxycarbonyl group $R_{17}$ include, for example, lower alkyl of 1 to 3 carbon atoms and lower alkoxy of 1 to 3 carbon atoms.

The lower alkyl or lower alkoxy $R_{18}$ is preferably a group of 1 to 3 carbon atoms, respectively.

Substituents on optionally substituted phenyl groups $R_{19}$ include, for example, lower alkyl of 1 to 3 carbon atoms, lower alkoxy of 1 to 3 carbon atoms, halogen, nitro, amino, hydroxy, optionally substituted aminomethyl, etc. Substituents on said optionally substituted aminomethyl may, for example, be carbamoyl, (2-oxo-3-benzylideneaminoimidazolidin-1-yl)carbonyl, (2-oxoimidazolidin-1-yl)carbonyl, etc. Substituents on optionally substituted phenoxy group $R_{19}$, for example, include lower alkyl of 1 to 3 carbon atoms, lower alkoxy of 1 to 3 carbon atoms, halogen, nitro, amino, hydroxy, aminomethyl. The optionally substituted lower alkyl group $R_{19}$ is preferably a group of 1 to 6 carbon atoms, the substituents being exemplified by halogen, hydroxy, cyano, trifluoromethyl, etc.

The alkenyl of optionally substituted alkenyl group $R_{19}$ may for example be vinyl, propenyl, etc., and the substituents may for example be carboxyl, cyano, etc. Examples of the heterocyclic ring of optionally substituted heterocyclic group $R_{19}$ include five- to six-membered heterocyclic groups including one sulfur atom or one to 4 nitrogen atoms and five- to six-membered heterocyclic groups including one sulfur atom and one nitrogen or oxygen atom. Thus, 2-thienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl, 1,4-oxathiinyl, etc. may be mentioned by way of example. Substituents on such optionally substituted heterocyclic group $R_{19}$ include, for example, lower alkyl of 1 to 3 carbon atoms, lower alkoxy of 1 to 3 carbon atoms, halogen, nitro, hydroxy, amino, carboxy, oxo, acylamino of 2 to 4 carbon atoms which may optionally be substituted by halogen, acyl of 2 to 4 carbon atoms and so forth.

The alkyl group of 1 to 12 carbon atoms, mentioned hereinbefore, may for example be methyl, trifluoromethyl, ethyl, n-propyl, isopropyl, n-butyl, isobutyl, sec-butyl, tert-butyl, pentyl, isopentyl, hexyl, isohexyl, heptyl, octyl, nonyl, decyl, undecyl, dodecyl or the like.

The lower alkyl group of 1 to 6 carbon atoms, mentioned hereinbefore, may for example be methyl, trifluoromethyl, ethyl, n-propyl, isopropyl, n-butyl, isobutyl, sec-butyl, tert-butyl, pentyl, isopentyl, hexyl, isohexyl, etc.

The lower alkyl group of 1 to 3 carbon atoms, also mentioned hereinbefore, may for example be methyl, trifluoromethyl, ethyl, n-propyl, isopropyl or the like.

The lower alkoxy group of 1 to 3 carbon atoms, mentioned hereinbefore, may for example be methoxy, ethoxy, n-propoxy, isopropoxy or the like.

The halogen includes chlorine, bromine, iodine and fluorine.

The lower alkylsulfonyl group containing 1 to 3 carbon atoms includes, for example, methylsulfonyl, ethylsulfonyl, n-propylsulfonyl, isopropylsulfonyl, etc.

The acylamino group of 2 to 4 carbon atoms includes, for example, acetylamino, propionylamino, n-butyrylamino isobutyrylamino, etc.

The acyloxy group of 2 to 10 carbon atoms includes, for example, acetoxy, n-propionyloxy, n-butyryloxy, isobutyryloxy, n-pentanoyloxy, n-hexanoyloxy, n-heptanoyloxy, n-octanoyloxy, n-nonanoyloxy, n-decanoyloxy, etc.

Referring to the aforementioned acyl group, the acyl group represented by the formula $R_6$—CO—(wherein $R_6$ has the same meaning as defined hereinbefore) includes, for example, 3-(2,6-dichlorophenyl)-5-methylisoxazol-4-yl-carbonyl, 4-ethyl-2,3-dioxo-1-piperazinocarbonyl, (2-oxoimidozolidin-1-yl)carbonyl, etc.

The acyl group represented by the formula:

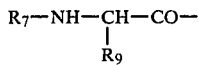

(wherein $R_7$ and $R_9$ have the same meanings as defined hereinbefore) includes, for example, D-alanyl, D-phenylalanyl, α-benzyl-N-carbobenzoxy-γ-D-glutamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltryptophyl-D-phenylglycyl, methylamidoasparaginyl-D-phenylglycyl, N-carbobenzoxymethylamidoasparaginyl-D-phenylglycyl, N-carbobenzoxy-D-phenylglycyl-D-phenylglycyl, 2-(2,3-diaminopropionamido)-2-phenylacetyl, D-alanyl-D-alanyl, 2-[2-amino-3-(N-methylcarbamoyl)propionamido]acetyl, 2-(2-amino-3-sulfamoylpropionamido)-2-phenylacetyl, 2-[2-amino-3-(4-ethyl-2,3-dioxo-1-piperazinocarboxamido)propionamido]-2-phenylacetyl, D-2-(4-ethyl-2,3-dioxo-1-piperazinocarboxamido)-2-(4-methoxyphenyl)acetyl, 4-ethyl-2,3-dioxo-1-piperazinocarbonyl, D-2-[2-(4-ethyl-2,3-dioxo-1-piperazinocarboxamido)-3-(N-methylcarbamoyl)propionamido]-2-phenylacetyl, D-2-[2-(4-ethyl-2,3-dioxo-1-piperazinocarboxamido)acetamido]-2-phenylacetyl, D-2-(3-sulfamoyl-2-benzyloxycarboxamidopropionamido)-2-phenylacetyl, D-2-[2-benzyloxycarboxamido-3-(4-methoxyphenyloxycarboxamido)propionamido]-2-phenylacetyl, 2-[2-benzyloxycarboxamido-3-(N-methylcarbamoyl)propionamido]acetyl, 2-(N-carbobenzoxy-D-phenylglycylamino)-3-(N-methylcarbamoyl)propionyl, N-carbobenzoxy-D-alanyl, 2-(benzyloxycarboxamido)-2-phenylacetyl, 2-(benzyloxycarboxamido-3-N-methylcarbamoylpropionyl, N-(4-ethyl-2,3-dithioxo-1-piperazinocarbonyl)-D-phenylglycyl, 2-(2-amino-4-thiazolyl)-2-(4-ethyl-2,3-dioxo-1-piperazinocarboxamido)acetyl, 2-(2-phenylacetoamido)propionyl, 2-(4-ethyl-2,3-dioxo-1-piperazinocarboxamido)-2-thienylacetyl, 2-(3-furfurylideneamino-2-oxoimidazolidine-1-carboxamido)-2-(4-hydroxyphenyl)acetyl, 2-(8-hydroxy-1,5-naphthyridine-7-carboxamido)-2-phenylacetyl, 2-(4-ethyl-2,3-dioxo-1-piperazinocarboxamido)-2-phenylacetyl, 2-(4-n-octyl-2,3-dioxo-1-piperazinocarboxamido)-2-phenylacetyl, 2-(4-ethyl-2,3-dioxo-1-piperazinocarboxamido)-2-(4-sulfoxyphenyl)acetyl, 2-(4-ethyl-2,3-dioxo-1-piperazinocarboxamido)-2-(4-chlorophenyl)acetyl, 2-(4-n-octyl-2,3-dioxo-1-piperazinocarboxamido)-2-(4-hydroxysulfonyloxyphenyl)acetyl, 2-(4-ethyl-2,3-dioxo-1-piperazinocarboxamido)-2-(4-methoxyphenyl)acetyl, 2-(4-ethyl-2,3-dioxo-1-piperazinocarboxamido)-2-(4-trimethylsilylphenyl)acetyl, 2-(4-ethyl-2,3-dioxo-1-piperazinocarboxamido)-2-(3-chloro-4-methoxyphenyl)acetyl, 2-(4-ethyl-2,3-dioxo-1-piperazinocarboxamido)-2-(3-chloro-4-hydroxysulfonyloxyphenyl)acetyl, 2-(4-ethyl-2,3-dioxo-1-piperazinocarboxamido)-2-(3-chloro-4-hydroxyphenyl)acetyl, 2-(4-ethyl-2,3-dioxo-1-piperazinocarbonyl)-2-(4-benzyloxyphenyl)acetyl, 2-(4-n-octyl-2,3-dioxo-1-piperazinocarboxamido)-2-(4-hydroxyphenyl)acetyl, N-(4-ethyl-2,3-dioxo-1-piperazinocarbonyl)glutaminyl, N-(4-ethyl-2,3-dioxo-1-piperazinocarbonyl)phenylalanyl, N-(4-ethyl-2,3-dioxo-1-piperazinocarbonyl)-D-alanyl, 2-(4-ethyl-2,3-dioxo-1-piperazinocarboxamido)-2-(4-hydroxyphenyl)acetyl, 2,2-bis(4-ethyl-2,3-dioxo-1-piperazinocarboxamido)acetyl, 2-(4-ethyl-2,3-dioxo-1-piperazinocarboxamido)-2-(1-cyclohexen-1-yl)acetyl, 2-(4-n-octyl-2,3-dioxo-1-piperazinocarboxamido)-2-thienylacetyl, 2-(4-ethyl-2,3-dioxo-1-piperazinocarboxamido)-2-(2-amino-4-thiazolyl)acetyl, 2-(4-ethyl-2,3-dioxo-1-piperazinocarboxamido)-2-(2-chloroacetamido-4-thiazolyl)acetyl, 2-(4-ethyl-2,3-dioxo-1-piperazinocarboxamido)-2-(2-methyl-4-thiazolyl)acetyl, 2-(4-ethyl-2,3-dioxo-1-piperazinocarboxamido)-2-(2-acetamido-4-thiazolyl)acetyl, 2-(4-n-octyl-2,3-dioxo-1-piperazinocarboxamido)-2-(2-amino-4-thiazolyl)acetyl, 2-(4-ethyl-2,3-dioxo-1-piperazinocarboxamido)-2-furylacetyl, 2-(4-ethyl-2,3-dioxo-1-piperazinocarboxamido)-2-(2-pyrrolyl)acetyl, 2-(4-ethyl-2,3-dithioxo-1-piperazinocarboxamido)-2-(4-hydroxyphenyl)acetyl, 2-(4-n-octyl-2,3-dioxo-1-piperazinocarboxamido)-2-(2-chloroacetamido-4-thiazolyl)acetyl, N-(4-ethyl-2,3-dioxo-1-piperazinocarbonyl)-D-methionyl, D-2-[4-(2-phenylethyl)-2,3-dioxo-1-piperazinocarboxamido]-phenylacetyl, D-2-(4-ethyl-2,3-dioxo-1-piperazinocarboxamido)-2-(4-benzoyloxyphenyl)acetyl, 2,5-bis(4-ethyl-2,3-dioxo-1-piperazinocarboxamido)pentanoyl, 2-(4-ethyl-2,3-dioxo-1-piperazinocarboxamido)-3-(N-methylcarbamoyl)propionyl, 2,3-bis(4-ethyl-2,3-dioxo-1-piperazinocarboxamido)propionyl, 2-(4-ethyl-2,3-dioxo-1-piperazinocarboxamido)-3-chloropropionyl, 2-(4-ethyl-2,3-dioxo-1-piperazinocarboxamido)-2-(4-n-octanoyloxyphenyl)acetyl, 2-(4-ethyl-2,3-dioxo-1-piperazinocarboxamido)-3-sulfamoylpropionyl, 2-(4-ethyl-2,3-dioxo-1-piperazinocarboxamido)-3-[(1-methyl-1H-tetrazol-5-yl)thio]propionyl, 2-(4-ethyl-2,3-dioxo-1-piperazinocarboxamido)acetyl, D-2-[4-(2-hydroxyethyl)-2,3-dioxo-1-piperazinocarboxamido]-2-phenylacetyl, D-2-[4-(2-chloroethyl)-2,3-dioxo-1-piperazinocarboxamido]-2-phenylacetyl, 2-(4-ethyl-2,3-dioxo-1-piperazinocarboxamido)-3-(ethoxycarbonylmethylcarbamoyl)propionyl, 2-(4-ethyl-2,3-dioxo-1-piperazinocarboxamido)-3-(thienylacetamido)propionyl, 2-(4-ethyl-2,3-dioxo-1-piperazinocarboxamido)-3-[2-(1H-tetrazol-1-yl)acetamido]propionyl, 2-(4-ethyl-2,3-dioxo-1-piperazinocarboxamido)-2-(1H-tetrazol-1-yl)-acetyl, 2-[(2-oxo-3-furfurylideneaminoimidazolidin-1-yl)carboxamido]-2-phenylacetyl, 2-[(2-oxo-3-furfurylideneaminoimidazolidin-1-yl)carboxamido]-2-(4-hydroxyphenyl)acetyl, 2-[(2-oxo-3-furfurylideneaminoimidazolidin-1-yl)carboxamido]-2-(4-hydroxysulfonyloxyphenyl)acetyl, 2-[[2-oxo-3-(thiophen-2-aldoimino)imidazolidin-1-yl]carboxamido]-2-phenylacetyl, 2-[(2-oxo-3-furfurylideneaminoimidazolidin-1-yl]carboxamido]-2-thienylacetyl, 2-(3-methylsulfonyl-2-oxoimidazolidine-1-carboxamido)-2-phenylacetyl, 2-[(2-oxo-3-furfurylideneaminoimidazolidin-1-yl)carboxamido]-2-(2-amino-4-thiazolyl)acetyl, 2-[(2-oxo-3-furfurylideneaminoimidazolidin-1-yl)carboxamido]-2-(2-chloroacetamido-4-thiazolyl)acetyl, 2-[(3-mesyl-2-oxoimidazolidin-1-yl)carboxamido]-2-phenylacetyl, 2-[[2-oxo-3-(thiophen-2-aldoimino)imidazolidin-1-yl]carboxamido]-2-thienylacetyl, 2-[(3-mesyl-2-oxoimidazolidin-1-yl)carboxamido]-2-thienylacetyl, D-2-[(2-oxo-3-furfurylideneaminoimidazolidin-1-yl)carboxamido]propionyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, 2-(3-furfurylideneamino-2-oxoimidazolidine-1-carboxamido)-2-phenylacetyl, 2-(coumarine-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4-thiazolyl)acetyl]-D-phenylglycyl, 2-(6-bromo-1-ethyl-1,4-dihydro-4-oxothieno[2,3-b]pyridine-3-carboxamido)-2-phenylacetyl, 2-[2-(2-amino-4-thiazolyl)acetamido]-2-phenylacetyl, 2-[2-(2-chloroacetamido-4-thiazolyl)acetamido]-2-phenylacetyl, 2-(2,5-dioxo-1,2,4-triazino-6-carboxamido)-2-thienylacetyl, 2-(2,4-dioxopyrimidino-5-carboxamido)-2-thienylacetyl, 2-(6-hydroxy-1,5-naphthyridinylcarboxamido)-2-phenylacetyl, 2-[2-(4-ethyl-2,3-dioxo-1-piperazinocarboxamido)-2-thienylacetamido]-2-phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxyprolylamino)-2-furylacetyl, α-(thienylmethylcarbonyl)alanyl, 2-(4-chlorobenzoylureido)-2-thienylacetyl, 2-(2-thienylacetamido)acetyl, N-benzylcarboxamido-D-alanyl, N-(4-hydroxybenzoyl)-D-alanyl, 2-(4-chlorobenzamido)propionyl, 2-(4-aminobenzamido)acetyl, N-(4-ethyl-2,3-dioxo-1-piperazinocarbonyl)methionyl-D-phenylglycyl, D-2-[2-(2,6-dichlorophenylthio)acetamido]-2-phenylacetyl, 2-(carbamoyl)amino-2-thienylacetyl, N-carbamoyl-D-phenylglycyl, 2-(3-methylcarbamoyl-3-methyl-1-ureido)-2-phenylacetyl, 2-(3-methylcarbamoyl-3-methyl-1-ureido)-2-(4-hydroxy)phenylacetyl, 2-(3-methylcarbamoyl-3-methyl-1-ureido)-2-thienylacetyl, 2-[3-(2-hydroxybenzoyl)-1-ureido]-2-phenylacetyl, 2-[3-(2-benzyloxybenzoyl)-1-ureido]-2-(4-hydroxysulfonyloxyphenyl)acetyl, 2-[3-(2-hydroxybenzoyl)-1-ureido]-2-(4-hydroxyphenyl)acetyl, 2-[3-(2-benzyloxybenzoyl)-1-ureido]-2-phenylacetyl, 2-[3-(2-benzyloxybenzoyl)-1-ureido]-2-(4-hydroxyphenyl)acetyl, D-2-[2-(benzoyloxycarboxamido)-2-(benzyloxycarbonyl)ethanesulfonamido]2-phenylacetyl, N-mesyl-D-phenylglycyl, etc.

The acyl group represented by the formula $R_{10}—R_{11}—CO—$ (wherein $R_{10}$ and $R_{11}$ have the same meanings as defined hereinbefore) includes, for example, N-[2-(2-amino-4-thiazolyl)-2-methoxyiminoacetyl]-D-alanyl, N-[2-(2-amino-4-thiazolyl)-2-methoxyiminoacetyl]-D-phenylglycyl, 2-(2-amino-4-thiazolyl)-2-[(2-(2-amino-4-thiazolyl)-2-methoxyiminoacetamido]acetyl, 2-(2-chloroacetamido-4-thiazolyl)-2-[2-(2-chloroacetamido-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-dichloroacetyloxyiminoacetyl, 2-[4-(γ-D-glutamyloxy)phenyl]-2-oxyiminoacetyl, 2-[4-(3-amino-3-carboxypropoxy)phenyl]-2-oxyiminoacetyl, 2-thienyl-2-(3-morpholinopropoxyimino)acetyl, 2-[2-(2-amino-4-thiazolyl)-2-methoxyiminoacetamido]-2-phenylacetyl, 2-[2-(2-chloroacetamido-4-thiazolyl)-2-methoxyiminoacetamido]-2-phenylacetyl, 2-[2-(2-amino-4-thiazolyl)-2-methoxyiminoacetamido[acetyl, etc.

The acyl group represented by the formula:

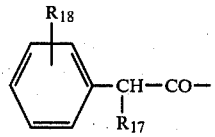

(wherein $R_{17}$ and $R_{18}$ have the same meanings as defined hereinbefore) includes, for example, α-sulfophenylacetyl, α-sulfoxyphenylacetyl, α-hydroxyphenylacetyl, α-sulfamoylphenylacetyl, α-phenoxycarbonylphenylacetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl, etc.

The acyl group of the formula:

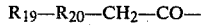

(wherein $R_{19}$ and $R_{20}$ have the same meanings as defined hereinbefore) includes, for example, cyanoacetyl, phenylacetyl, phenoxyacetyl, trifluoromethylthioacetyl, cyanomethylthioacetyl, 1H-tetrazoyl-1-acetyl, 2-thienylacetyl, 2-(2-amino-4-thiazolyl)acetyl, 2-(2-chloroacetamido-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-[2-(2-oxoimidazolidin-1-yl)carbonylaminomethylphenyl]acetyl, 2-[2-(2-oxo-3-benzylideneaminoimidazolidin-1-yl)carbonylaminomethylphenyl]acetyl, 2-(5,6-dihydro-1,4-oxathiin-2-yl)acetyl, 2-(2,5-dioxopyrrolidin-3-yl)acetyl, 2-succinimidoacetyl, 2-(1-acetyl-2,4-dioxoimidazolidin-3-yl)acetyl, etc.

The amino and/or carboxyl group in the acyl group described above may optionally carry a protective group.

Such amino-protecting groups include those groups which will be mentioned hereinafter as "amino-protecting groups." The carboxyl-protecting groups include any and all groups, such as ester and silyl residues, which are usually employed for the protection of carboxyl in the chemistry of β-lactams and in organic chemistry in general. Thus, for example, the ester residues may be methyl, ethyl, propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, trimethylsilyl, dimethylsilyl, acetylmethyl, p- nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxide-2-methyl, methylsulfinylmethyl, bis(p-methoxyphenyl)methyl, 2-cyano-1,1-dimethylethyl, etc. This invention provides new monocyclic compounds and the selection of such protective groups is only marginal to the gist of this invention. Especially, benzyl, $\beta,\beta,\beta$-trichloroethyl, p-nitrobenzyl or p-methoxybenzyl is preferable.

The "amino-protecting group" which is used to protect the amino group in the practice of this invention may expediently be one of those groups used in the field of $\beta$-lactam chemistry or in the field of peptide synthesis. Thus, use may be made, for example, of aromatic acyl groups such as phthaloyl, p-nitrobenzoyl, p-tert-butylbenzoyl, p-tert-butylbenzenesulfonyl, benzenesulfonyl, toluenesulfonyl, etc.; aliphatic acyl groups such as formyl, acetyl, propionyl, monochloroacetyl, dichloroacetyl, trichloroacetyl, methanesulfonyl, ethanesulfonyl, trifluoroacetyl, maloyl, succinyl, etc.; esterified carboxyl groups such as methoxycarbonyl, ethoxycarbonyl, t-butoxycarbonyl, isopropoxycarbonyl, 2-cyanoethoxycarbonyl, $\beta,\beta,\beta$-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl; methylene groups such as (hexahydro-1H-azepin-1-yl)methylene; sulfonyl groups such as 2-amino-2-carboxyethylsulfonyl, etc.; and amino-protecting groups other than acyl groups, such as trityl, 2-nitrophenylthio, benzylidene, 4-nitrobenzylidene, di- or trialkylsilyl, benzyl, p-nitrobenzyl, etc. The present invention is not particularly concerned with limitations on the selection of amino-protecting groups nor regarding the carboxyl-protecting groups. Especially, monochloroacetyl, benzyloxycarbonyl, p-methoxybenzyloxycarbonyl or p-nitrobenzyloxycarbonyl is preferable.

The azetidine derivative (I) according to this invention can be produced, for example by the following procedures.

(Procedure 1)

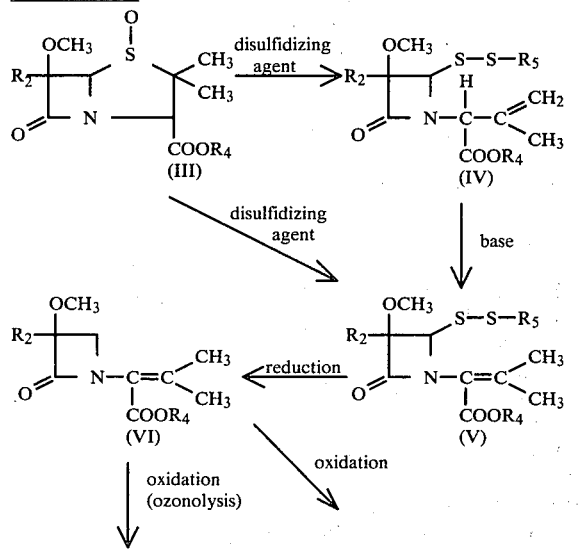

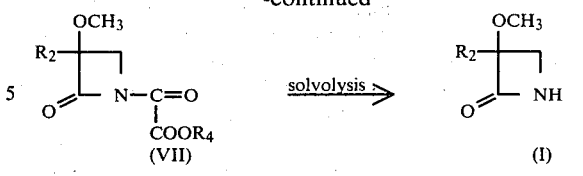

(Procedure 2)

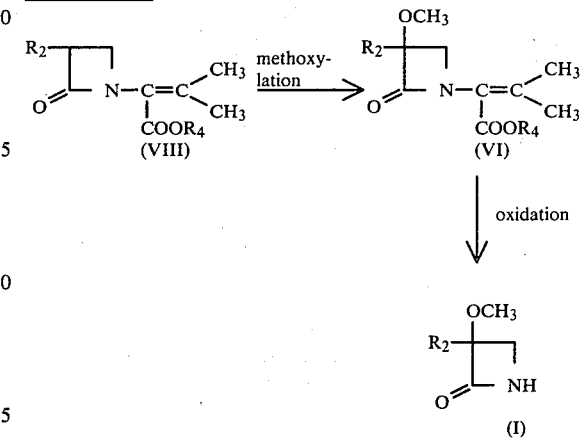

Regarding the symbols used in the above reaction formulas representing the two procedures (1) and (2), $R_2$ has the same meaning as defined hereinbefore; $R_4$ is an ester residue and $R_5$ is a thiol residue.

Exemplary species of the members defined in the above definitions are as follows.

The ester residue $R_4$ includes, for example, methyl, ethyl, propyl, isopropyl, n-butyl, t-butyl, pentyl, cyclopentyl, cyclohexyl, benzyl, p-nitrobenzyl, benzhydryl, alkoxyalkyl, alkanoyloxymethyl, alkenyl, trichloroethyl, methylsulfonylethyl, benzoylmethyl, methoxybenzyl, trityl, methylthiomethyl, pivaloyloxymethyl, α-acetoxybutyl, etc.

The thiol residue $R_5$ includes, for example, alkyl groups (e.g. methyl, ethyl, propyl, isopropyl, n-butyl, t-butyl, isobutyl, n-amyl, vinyl, 1-isopropenyl, etc.), substituted alkyl groups (e.g. methoxymethyl, ethoxymethyl, benzyl, phenethyl, xylylmethyl, p-chlorobenzyl, p-nitrobenzyl, p-methoxybenzyl, etc.), unsubstituted and substituted aryl groups (e.g. phenyl, xylyl, tolyl, naphthyl, chlorophenyl, nitrophenyl, methoxyphenyl, etc.), heterocyclic groups (e.g. benzothiazolyl, benzoxazolyl, thiazolyl, thiadiazolyl, oxazolyl, thienyl, pyridyl, oxadiazolyl, oxatriazolyl, imidazolyl, benzimidazolyl, triazolyl, tetrazolyl, etc.), acyl groups (e.g. acetyl, propionyl, benzoyl, thioacetyl, thiopropionyl, thiobenzoyl, etc.), carbamoyl groups (e.g. methylcarbamoyl, dimethylcarbamoyl, phenylcarbamoyl, etc.), the corresponding and other thiocarbamoyl groups, and groups of the formula:

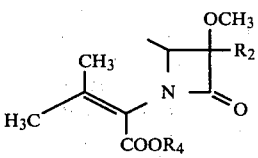

The above-mentioned procedures for producing the 3-methoxy-2-oxoazetidine derivatives (I) of this invention will be described in detail.

Procedure (1)

This method is related to a fundamental synthetic method for optically active 3-methoxy-2-oxoazetidine derivatives (I).

The compound (III) used as a starting material can be easily prepared, for example, by the method described in Journal of the American Chemical Society 95, 2401 (1973) or a method analogous thereto. In the first stage, compound (III) is reacted with a disulfidizing agent. The term "disulfidizing agent" is used herein to include all the reagents that are capable of disulfidizing the sulfur in 1-position of compound (III) and, in particular, thiol compounds of the formula $R_5$-SH and disulfides of the formula $R_5$-S-S-$R_5$ ($R_5$ has the same meaning as defined hereinbefore).

This reaction is carried out in the absence of a solvent or in an appropriate solvent. The solvent includes, for example, dioxane, N,N-dimethylacetamide, N,N-dimethylformamide, benzene, toluene, tert-butanol, isopropanol, methyl ethyl ketone, etc., mixtures of such solvents, and other solvents which will not interfere with the reaction. While the reaction temperature is not particularly critical, it is normally advantageous to carry out the reaction at a temperature between 70° C. and 150° C.

When a disulfide compound of the formula $R_5$-S-S-$R_5$ is employed as said disulfidizing agent, the reaction is catalytically accelerated by the presence of an acid or a base. This acid includes, for example, sulfuric acid, phosphoric acid, hydrochloric acid and other mineral acids, p-toluenesulfonic acid, methanesulfonic acid, phenylphosphonic acid, acetic acid, formic acid and other organic acids, and Lewis acids such as ferric chloride, zinc chloride, boron trifluoride, etc. When such an acid is employed, there is predominantly obtained a 1-(2'-propenyl)azetidine (IV) which contains a double bond in 2'-position. The base mentioned above includes, for example, pyridine, quinoline, N,N-dimethylaniline, triethylamine, etc. In this case, depending on the reaction solvent, time, temperature, etc., there is obtained a 1-(1'-propenyl)-azetidine (V) having a double bond in 1'-position in addition to the 1-(2'-propenyl)-azetidine (IV). This 1-(1'-propenyl)-azetidine (V) can also be easily obtained by treating 1-(2'-propenyl)-azetidine (IV) with a base. The reaction according to this procedure is preferably carried out in streams of an inert gas such as nitrogen, helium or the like. The useful molar ratio of disulfidizing agent to starting compound (III) depends on the S-nucleophilicity of the disulfidizing agent used but, generally speaking, about 1 to about 10 equivalents of said agent are employed. After completion of the reaction, the product compound (IV) can be isolated in optional purity by the purification procedures known per se, e.g. extraction with solvents, recrystallization, chromatography, etc.

The compound (IV), on treatment with a base, yields the compound (V). The base used for this purpose may be the above-mentioned base which can be used as catalyst in the reaction between compound (IV) and disulfidizing agent. In carrying out this reaction, the base need not be employed in a large amount. Thus, relative to compound (IV), about 0.01 to about 0.2 mol equivalent is sufficient. The reaction is generally carried out in a solvent such as dichloromethane, chloroform, benzene, toluene, tert-butanol, methanol, ethanol, tetrahydrofuran, dioxane, methyl ethyl ketone, N,N-dimethylacetamide, N,N-dimethylformamide, etc. or a mixture of such solvents. Any other solvent that will not interfere with the reaction may also be employed. While the reaction temperature is not particularly critical, the reaction proceeds at room temperature in many instances. The product derivative (V) in which $R_5$ is a group of the formula:

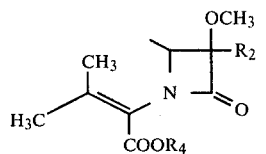

is a compound which is obtained simultaneously or partially in this reaction step and can be converted to compound (VI) by treatment with a reducing agent.

Then, compound (V) is subjected to a reductive desulfurization reaction. The reductive desulfurizing agent used for this purpose may, for example, be Raney nickel, Raney cobalt or the like. This reaction is usually carried out in a solvent. The solvent includes, for example, methanol, ethanol, propanol, tetrahydrofuran, dioxane, ethyl acetate, water, etc., although other common organic solvents which do not interfere with the reaction may also be employed. This reaction proceeds readily under mild conditions, e.g. at room temperature to about 80° C.

The resulting compound (VI) is oxidized to compound (I). This oxidation reaction includes an oxidization reaction with an oxidizing agent and a subsequent solvolysis with a solvent or a basic or acidic catalyst.

The oxidizing agent used in the above oxidation reaction includes, for example, ozone, alkali metal permanganate (e.g. potassium permanganate, sodium permanganate, etc.), alkaline earth metal permanganate (e.g. barium permanganate, etc.), osmium tetraoxide, lead tetraacetate, etc. This oxidation reaction is usually carried out in a solvent. This solvent includes, for example, tetrahydrofuran, dioxane, N,N-dimethylformamide, N,N-dimethylacetamide, benzene, acetone, pyridine, methanol, ethanol, propanol, butanol, water, chloroform, dichloromethane, carbon tetrachloride, etc. It may be a mixture of such solvents. The proportion of the oxidizing agent relative to compound (VI) may be about 1 to about 4 molar equivalents, preferably about 1 to 1.2 molar equivalents, although excess ozone if it is used may be employed. While the reaction temperature is not particularly critical, the reaction usually proceeds under cooling or at room temperature. The reaction normally goes to completion within a short time. When a permanganate, for instance, is employed as the oxidizing agent, it is preferable to employ a buffer solution such as phosphate buffer and carry out the reaction in the neutral pH region so as to minimize the decomposition of starting compound (VI) or/and product compound (I). When ozone is used as said oxidizing agent, the conversion of compound (VI) to compound (VII) can be effected by ozonolysis e.g. by carrying out the reaction in a solvent such as chloroform, dichloromethane or carbon tetrachloride, followed by removing the excess ozone and decomposing the ozonide of compound (VI) with dimethyl sulfide.

The conversion of compound (VII) to compound (I) is effected by subjecting compound (VII) to solvolysis. This reaction is carried out in a suitable solvent and may be optionally conducted with the aid of a basic or acidic catalyst. The base used in such a procedure includes, for instance, inorganic bases such as the hydroxides, carbonates, etc. of alkali metals such as lithium, potassium, sodium, etc. or alkaline earth metals such as calcium, magnesium, etc.; organic bases such as metal alkoxides, organic amines, quaternary ammonium salts, etc.; basic ion exchange resins and so forth. The acid used in a similar manner includes inorganic acids and their salts such as hydrochloric acid, sulfuric acid, phosphoric acid, zinc chloride, zinc sulfate, ferric chloride, ferric sulfate, etc., organic acids such as formic acid, acetic acid, p-toluenesulfonic acid, trifluoroacetic acid, etc., silica gel, acidic ion exchange resins and so forth. The solvent used for this reaction includes, for example, water, methanol, ethanol, propanol, tetrahydrofuran, dioxane, ethyl acetate, etc. as well as mixtures thereof. Any other solvent that will not interfere with the reaction may also be employed. This reaction usually proceeds easily under mild conditions, e.g. under cooling to a slightly elevated temperature.

The reaction product in each step can be separated in optional purity by purification procedures known per se, e.g. extraction with solvents, recrystallization, chromatography, etc.

Procedure (2)

This procedure relates to a fundamental route of synthesis for the production of optically inactive 3-methoxy-2-oxoazetidine derivative (I).

The starting compound (VIII) can be easily prepared by the method described in Molecular Modification in Drug Design 45, 15 (1964) or a method analogous thereto.

The methoxylation reaction of compound (VIII) to compound (VI) is carried out by reacting an alkali metal salt of methanol, which is of the formula $MOCH_3$ (wherein M is an alkali metal), and a halogenating agent with the compound (VIII) in the presence of methanol. As examples of the alkali metal salt of methanol may be mentioned lithium methoxide, sodium methoxide, potassium methoxide, etc. The halogenating agent is halogen compound capable of acting as a positive-halogen donor, e.g. halogen (chlorine, bromine, etc.), N-haloimides (N-chlorosuccinimide, etc.), haloamides (N-chloroacetamide, N-bromoacetamide, etc.), N-halosulfonamides (N-chlorobenzenesulfonamide, N-chloro-p-toluenesulfonamide, etc.), 1-halobenzotriazoles, organic hypochlorites (t-butyl hypochlorite, etc.). This reaction is carried out in a solvent. Examples of the solvent include tetrahydrofuran, dioxane, dichloromethane, chloroform, acetonitrile, methanol, N,N-dimethylformamide, N,N-dimethylacetamide, etc. as well as various mixtures thereof. Any other solvent that will not interfere with he contemplated reaction may likewise be employed. To carry out the reaction, the starting compound (VIII) is dissolved or suspended in the above-mentioned solvent and, then, the alkali metal salt of methanol, methanol and halogenating agent are added. The desirable proportions of these agents, relative to each mol of starting compound (VIII), are not less than 1 mol of methanol, about 1 to 3.5 mols of the alkali metal salt of methanol and about 1 to 2 mols of halogenating agent. The reaction proceeds readily under cooling or at room temperature to about 30° C. The reaction can be quenched by making the reaction system acidic. The suitable acid for quenching the reaction may for example be formic acid, acetic acid or trichloroacetic acid. After the reaction has thus been quenched, any excess halogenating agent can be removed by treatment with a reducing agent such as sodium thiosulfate or a trialkyl phosphite, for instance.

After completion of the above reaction, the product compound (VI) can be isolated in an optional purity by conventional separation-purification procedures, for example by extraction with a solvent, recrystallization, chromatography, etc.

The compound (VI) is then subjected to procedures similar to the oxidation procedures described hereinbefore in connection with the conversion of compound (VI) to compound (I), whereby an optically inactive form of compound (I) is obtained.

The acylation reaction according to this invention is accomplished by reacting 3-amino-3-methoxy-2-oxoazetidine with an acylating agent containing an acyl group represented by $R^3$.

The acylating agent used in this reaction may for example be an organic carboxylic acid containing such an acyl group $R^3$ or a reactive derivative of such acid. The reactive derivative of organic acid includes, for example, the acid anhydride, activated amide, activated ester or the like. More specifically, the following reactive derivatives of organic acids may be mentioned.

(1) Acid anhydrides

The acid anhydrides include, for example, hydrogen halides (e.g. hydrochloric acid, hydrobromic acid, etc.) mixed acid anhydrides, monoalkyl carbonic acid mixed acid anhydrides, aliphatic carboxylic acid mixed acid anhydrides (mixed acid anhydrides with e.g. acetic acid, pivalic acid, valeric acid, isopentanoic acid, trichloroacetic acid, etc.), aromatic carboxylic acid mixed acid anhydrides (mixed acid anhydrides with e.g. benzoic acid, etc.), symmetric acid anhydrides, etc.

(2) Activated amides

The activated amides include, for example, the amides with pyrazole, imidazole, 4-substituted-imidazole, dimethylpyrazole, benzotriazole, etc.

(3) Activated esters

The activated esters include, for example, methyl ester, ethyl ester, methoxymethyl ester, propargyl ester, 4-nitrophenyl ester, 2,4-dinitrophenyl ester, trichlorophenyl ester, pentachlorophenyl ester, mesylphenyl ester, esters of said carboxylic or other acids with 1-hydroxy-1H-2-pyridone, N-hydroxysuccinimide, N-hydroxyphthalimide, etc.

The said reactive derivative of organic acid is selected according to the type of acid chosen and when a free acid is used as the acylating agent, the reaction is desirably carried out in the presence of a condensing agent. The condensing agent includes, for example, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.

This acylation reaction is generally carried out in a solvent. The solvent includes, for example, water, acetone, dioxane, acetonitrile, dichloromethane, chloroform, dichloroethane, tetrahydrofuran, ethyl acetate, dimethylformamide, pyridine, etc. as well as the common organic solvents which do not interfere with the reaction. These solvents, if they are hydrophilic, may be used in a mixture with water.

Further, the acylation reaction can be carried out in the presence of a base, for example alkali metal carbonates, trialkylamines (e.g. trimethylamine, triethylamine, tributylamine, N-methylmorpholine, N-methylpiperidine, etc.), N,N-dialkylaniline, N,N-dialkylbenzylamine, pyridine, picoline, lutidine, 1,5-diazabicyclo[4,3,0]non-5-ene, 1,4-diazabicyclo[2,2,2]octane, 1,8-diazabicyclo[5,4,4]undecene-7, etc. The base, as well as said condensing agent, may be used as the solvent as well, only if it is liquid. The reaction temperature is not particularly critical and, in many cases, the reaction is carried out under cooling to room temperature.

The removal of the protective group from the azetidine derivative (V) can be effected by a choice of the hitherto-known procedures, the choice depending on the type of protective group. Thus, for example, the method may comprise the use of an acid, a base or hydrazine, or may be a reductive method or a method comprising permitting an iminohalogenating agent to act on the substrate compound and, then, an imminoetherifying agent to act thereon and, finally and if necessary, hydrolyzing the same. In the method employing an acid, while the choice depends on the type of protective group and other conditions, the acid may for example be an inorganic acid (e.g. hydrochloric acid, sulfuric acid, phosphoric acid, etc.), an organic acid (e.g. formic acid, acetic acid, trifluoroacetic acid, propionic acid, benzenesulfonic acid, p-toluenesulfonic acid, etc.) or an acidic ion exchange resin. In the method involving the use of a base, while the choice depends on the type of protective group and other conditions, the base may for example be an inorganic base such as the hydroxide or carbonate of an alkali metal (e.g. sodium, potassium, etc.) or alkaline earth metal (e.g. calcium, magnesium, etc.), an alkali metal alkoxide, an organic base (e.g. organic amines, quaternary ammonium salts, etc.) or a basic ion exchange resin.

When, in the above methods involving the use of a base or an acid, a solvent is employed, it is generally desirable, in many cases, to use a hydrophilic organic solvent, water or a mixture thereof.

The reductive method, while the choice depends on the type of protective group and other conditions, may be a method employing a metal (e.g. tin, zinc, etc.) or a metal compound (e.g. chromous dichloride, chromous acetate, etc.) and an organic, inorganic or other acid (e.g. acetic acid, propionic acid, hydrochloric acid, etc.), or a method involving the presence of a metal catalyst for catalytic reduction. As examples of the catalyst used for such catalytic reduction, there may be mentioned platinum catalysts such as platinum wire, platinum sponge, platinum black, platinum oxide, colloidal platinum, etc., palladium catalysts such as palladium sponge, palladium black, palladium oxide, palladium-barium sulfate, palladium-barium carbonate, palladium-carbon, palladium-silica gel, colloidal palladium, etc., and nickel catalysts such as reduced nickel, nickel oxide, Raney nickel, Urushibara nickel, etc.

In the reductive method employing a metal and an acid, the combination of a metal compound, e.g. a compound of iron, chromium or the like, with an inorganic acid, e.g. hydrochloric acid, or an organic acid, e.g. formic acid, acetic acid, propionic acid or the like, is employed. The reductive procedure is normally carried out in a solvent. In the case of catalytic reduction, alcohols such as methanol, ethanol, propanol, isopropyl alcohol, etc. and ethyl acetate, etc. are commonly employed. In the procedure involving the use of a metal and an acid, the solvent is usually water, acetone or the like, but when the acid is liquid, it may be utilized as the solvent as well.

The reaction is usually carried out under conditions of cooling to warming, preferably at a temperature of the range from about 0° C. to about 30° C.

Referring to the procedure comprising the use of an iminohalogenating agent and, then, an iminoetherifying agent, followed by hydrolysis to remove the protective group, the iminohalogenating agent may for example be phosphorus trichloride, phosphorus pentachloride, phosphorus tribromide, phosphorus pentabromide, phosphorus oxychloride, thionyl chloride or phosgene. The reaction temperature is not critical and, in many cases, the reaction is carried out under conditions of room temperature to cooling. The iminoetherifying agent which is then permitted to act on the resultant reaction product may for example be an alcohol or a metal alkoxide. Thus, the alcohol includes, for example, alkanols such as methanol, ethanol, propanol, isopropyl alcohol, n-butanol, tert-butanol, etc.; and compounds such that the alkyl moieties of such alkanols as mentioned above have been substituted by alkoxy groups such as methoxy, ethoxy, propoxy, isopropoxy, butoxy, etc. The metal alkoxide includes, for exmaple, alkali metal alkoxides (sodium alkoxides, potassium alkoxides, etc.) and alkaline earth metal alkoxides (calcium alkoxides, barium alkoxides, etc.) as may be derived from the above-mentioned and other alcohols.

When, for example, the protective group is an organic carboxylic acid residue and the carbon atom adjacent to its carbonyl group carries a certain substituent such as a free amino, hydroxyl, mercapto, carboxyl or sulfo group, it is advantageous first to carry out a treatment of enhancing the adjacent group effect of such group so as to increase the reactivity of the carbonyl group before carrying out the removal of the protective group. In this connection, the case in which the substituent group on the carbon atom adjacent to said carbonyl group is a free amino group will be described by way of illustration. Thus, the free amino group may be converted to a thioureido group and, then, the necessary deacylation reaction is carried out. This and other procedures known in the art of cleavage of peptide bonds can be utilized to remove the protective group.

The temperature for this reaction is not especially critical but may be suitably selected according to the type of protective group and the method then applied for removing the protective group. It is preferable, after all, that the reaction is carried out under cooling to a slightly elevated temperature.

There are cases in which the derivative in the carboxyl function of the compound wherein $R_1$ is a group containing such a carboxyl group is transformed into a carboxyl group in the course of this reaction and such cases are also subsumed in the concept and ambit of this invention.

The compound (I) thus obtained by removal of the protective group can be converted, if desired, to a desired salt thereof in a conventional manner.

There also are cases in which the compound (I) exists in diastereo-isomers or optical-isomers. In such cases, both the respective isomers and mixtures thereof are included in the scope of this invention.

These isomers, either respectively or in mixtures, can be used as intermediates for the synthesis of medicines. Where such isomers are obtained as a mixture, it may be separated, if desired, into the component isomers by optical resolution procedures or by the purification procedures known per se, e.g. extraction with solvent, recrystallization, chromatography, etc.

The product compound (I) according to this invention is of value as an intermediate for the synthesis of useful medicines.

For example, subjecting the compound (I) to a sulfonation reaction yields a compound of the following general formula (IX) which can be used as a drug in the treatment of bacterial infections.

wherein $R_1$ has the same meaning as defined hereinbefore.

The sulfonation reaction referred to above is a reaction by which a sulfo group is introduced into the substrate compound and can be carried out, for example by reacting compound (I) with sulfur trioxide or a reactive derivative of sulfur trioxide.

As examples of said reactive derivative of sulfur trioxide may be mentioned sulfur trioxide-pyridine, sulfur trioxide-dioxane, sulfur trioxide-trimethylamine, sulfur trioxide-chlorosulfonic acid complexes, and other addition compounds of $SO_3$. To accomplish this reaction, about 1 to about 5 molar equivalents, preferably about 1 to about 2 molar equivalents, of sulfur trioxide or said reactive derivative of sulfur trioxide is added to every mol of compound (I). The reaction temperature is about 0° to about 80° C. and preferably about 10 to about 40° C. The above reaction may be carried out in a solvent. This solvent includes, for example, water, ethers (e.g. dioxane, tetrahydrofuran, diethyl ether, etc.), esters (e.g. ethyl acetate, ethyl formate, etc.), halogenated hydrocarbons (e.g. chloroform, dichloromethane, etc.), hydrocarbons (e.g. benzene, toluene, n-hexane, etc.) and amides (e.g. dimethylformamide, dimethylacetamide, etc.). These and other common solvents can be employed alone or as a mixture. After the reaction, the reaction mixture can be subjected to a purification procedure known per se, e.g. extraction with a solvent, recrystallization, chromatography, etc., whereby the compound (IX) can be obtained in an optional purity.

Referring to compound (IX), wherein $R_1$ is a protected amino group, the protective group may be removed if necessary. The removal of this protective group can be accomplished in the same manner as described hereinbefore.

The compound (IX), which contains a sulfo group, is generally capable of forming a salt with a base. Therefore, the compound (IX) may then be isolated as a salt which, in turn, may be converted to the free form or to a different salt. The free compound (IX) may of course be converted to a salt. The base mentioned above may be an inorganic base, e.g. lithium, potassium, sodium, calcium, ammonium, etc. or an organic base, e.g. pyridine, collidine, triethylamine, triethanolamine, etc.

To convert the salt form of compound (IX) into the free compound (IX), a method using an acid, for example, can be employed. The type of acid varies with different protective groups and other conditions. However, such inorganic acids as hydrochloric acid, sulfuric acid, phosphoric acid, etc. and such organic acids as formic acid, acetic acid, p-toluene-sulfonic acid, etc. are generally employed. Aside from the type of acids mentioned above, acidic ion exchange resins are also useful.

The solvent may for example be acetone, tetrahydrofuran, methanol, ethanol, dioxane or the like, water, or a mixture of water and such a solvent.

The compound (IX) may exist as optical isomers (e.g. D- and L-isomers). In such cases, the respective isomers and their mixtures are also included in the scope of this invention. These isomers, respectively or as mixtures, can be used as medicines.

When such mixtures of isomers are recovered as products, each mixture may be resolved into the component isomers by the conventional optical resolution method.

The compound (IX) thus obtained is useful as a drug, being active against certain gram-positive and gram-negative bacteria. By way of example, the compound is active against the following microorganisms.

TABLE 1

Antimicrobial Spectrum

| Test organism | Medium* | Minimum inhibitory concentration (μg/ml) of Compound** |
|---|---|---|
| Staphylococcus aureus FDA209P | TSA | 100 |
| Escherichia coli NIHJ JC-2 | TSA | 50 |
| Escherichia coli O-111 | TSA | 12.5 |
| Klebsiella pneumoniae DT | TSA | 12.5 |
| Enterobacter cloacae IFO 12937 | TSA | >100 |
| Serratia marcescens IFO 12648 | TSA | 50 |
| Proteus vulgaris IFO 3988 | TSA | 12.5 |
| Proteus mirabilis IFO 3849 | TSA | 50 |
| Pseudomonas morganii IFO 3168 | TSA | >100 |
| Pseudomonas aeruginosa U 31 | TSA | >100 |
| Candida albicans TA | TSA | >100 |
| Streptococcus pyogenes E-14 | B-TSA | 50 |
| Streptococcus pyogenes S-8 | B-TSA | 50 |
| Corynebacterium diphtheriae Toronto | B-TSA | 50 |

*Medium:
TSA = Trypticase soy agar [Baltimore Biologicals (U.S.A.)]
B-TSA = Blood trypticase soy agar
**Compound = Sodium 3-[D-(−)-N—(4-ethyl-2,3-dioxo-1-piperazinocarbonyl)-phenylglycinamido-3-methoxy-2-oxoazetidine-1-sulfonate The acute toxicity ($LD_{50}$) of compound (IX) in mice, by intravenous administration, is generally not less than 500 mg/kg.

The compound (IX) is of value in the treatment of mammalian animals (e.g. mouse, rat, human being, etc.) infected by the above-mentioned and other microorganisms.

As a bacterial infection remedy, the compound (IX) can be applied, for example, to the treatment of respiratory organ infections, urinary tract infections, suppurative diseases, bile duct infections, intestinal infections, gynecologic and obstetric infections, surgical infections, etc. in the above-mentioned mammals. The daily dose is about 20 to about 200 mg/kg body weight as compound (IX) and is preferably administered in 2 to 4 portions daily, i.e. about 5 to about 100 mg/kg body weight per dose. The compound (IX), or a physiologically acceptable salt thereof, can be orally administered in such dosage forms as tablets, capsules, drops, etc. which can be prepared by the established pharmaceutical procedures. The compound and salt each can also be worked up into injectable preparations by the routine pharmaceutical procedure, for instance, and after mixing with a sterile vehicle which is obtainable by the conventional procedure, be administered parenterally.

This invention will be further described by way of the following reference and working examples.

REFERENCE EXAMPLE 1

A mixture of 4.1 g of methyl 6β-benzyloxycarboxamido-6α-methoxypenicillanate-1-oxide and 10 ml of n-amylmercaptan is stirred at 110° C. for 24 hours. The excess n-amylmercaptan is distilled off and the residue is chromatographed on a column of silica gel [eluted with n-hexane-ethyl acetate (2:1)] to give 2.5 g of methyl 4β-n-amyldithio-3β-benzyloxycarboxamido-3α-methoxy-2-oxoazetidine-1-(α-isopropenyl)acetate.

IR$\nu_{max}^{KBr}$ cm$^{-1}$; 3300, 1767, 1736.

NMR(CDCl$_3$, ppm); 0.93(t, —CH$_3$), 1.2–1.7(m, —CH$_2$—), 1.92(s, —CH$_3$), 2.76(t, —S—CH$_2$—), 3.60(s, —CH$_3$), 3.83(s, —CH$_3$), 4.92(s, —CH—), 5.07(s, —CH—), 5.20(m, =CH$_2$), 5.23(s, —CH$_2$—), 5.66(s, —NH—), 7.42(s, aromatic H).

REFERENCE EXAMPLE 2

To a solution of 2.3 g of methyl 4β-n-amyldithio-3β-benzyloxycarboxamido-3α-methoxy-2-oxoazetidine-1-(α-isopropenyl)acetate in 60 ml of methylene chloride is added 0.15 g of triethylamine and the mixture is stirred at room temperature for 1.5 hours. The solvent is distilled off and the residue is chromatographed on a column of silica gel [eluted with n-hexane-ethyl acetate (4:1)] to give 2.2 g of methyl 4β-n-amyldithio-3β-benzyloxycarboxamido-3α-methoxy-2-oxoazetidine-1-(α-isopropylidene)acetate.

IR$\nu_{max}^{KBr}$ cm$^{-1}$; 3300, 1768, 1735.

NMR(CDCl$_3$, ppm); 0.92(t, —CH$_3$), 1.15–1.98(m, —CH$_2$—), 2.08(s, —CH$_3$), 2.32(s, —CH$_3$), 2.65(t, —S—CH$_2$—), 3.64(s, —CH$_3$), 3.83(s, —CH$_3$), 5.23(s, —CH$_2$—), 5.32(s, —CH—), 5.70(s, NH), 7.42(s, aromatic H).

REFERENCE EXAMPLE 3

To a solution of 2.1 g of methyl 4β-n-amyldithio-3β-benzyloxycarboxamido-3α-methoxy-2-oxoazetidine-1-(α-isopropylidene)acetate in 40 ml of ethanol is added 18 ml of Raney nickel, followed by stirring at room temperature for one hour. The Raney nickel is filtered off, and the filtrate is condensed to dryness. The residue is chromatographed on a column of silica gel [eluted with n-hexane-ethyl acetate (3:1)] to obtain 0.62 g of methyl 3-benzyloxycarboxamido-3-methoxy-2-oxoazetidine-1-(α-isopropylidene)acetate.

IR$\nu_{max}^{KBr}$ cm$^{-1}$; 1760, 1718, 1510.

NMR(CDCl$_3$, ppm); 1.93(s, CH$_3$), 2.20(s, CH$_3$), 3.50(s, CH$_3$), 3.70(s, CH$_3$), 3.91(dd, J=6 Hz, C$_4$-H), 5.13(s, —CH$_2$—), 6.03(s, NH), 7.26(aromatic H).

REFERENCE EXAMPLE 4

A solution of 47.5 g of methyl 3-phenylacetamido-2-oxoazetidine-1-(α-isopropylidene)acetate in 750 ml of methylene chloride is cooled to a temperature below −70° C., followed by the addition of 93.7 g of finely divided phosphorus pentachloride and 71.2 g of pyridine. The mixture is stirred under ice-cooling for 70 minutes. The reaction mixture is cooled to −70° C. and after addition of 150 ml of n-butanol, the temperature is returned gradually to 0° C. After an hour, 300 ml of ice-water is added and the water layer is taken. The solution is adjusted to pH 6.2 with sodium hydrogen carbonate and extracted with chloroform. The extract is condensed to obtain 56 g of methyl 3-amino-2-oxoazetidine-1-(α-isopropylidene)acetate.

IR$\nu_{max}^{CHCl_3}$ cm$^{-1}$; 3400, 3330, 1750, 1720.

NMR(CDCl$_3$, ppm); 1.90(s, —CH$_3$), 2.04(br. s, —NH$_2$), 2.16(s, —CH$_3$), 3.2–3.9(m, —CH$_2$—), 3.73(s, —CH$_3$—), 4.28(m, —CH—).

REFERENCE EXAMPLE 5

To a solution of 58 g of methyl 3-amino-2-oxoazetidine-1-(α-isopropylidene)acetate in 240 ml of methylene chloride are added 120 ml of propylene oxide and, then, 56.3 g of carbobenzoxy chloride with stirring and under ice-cooling. The reaction mixture is returned to room temperature and, then, stirred for 30 minutes. The solvent is distilled off to obtain 82.6 g of methyl 3-benzyloxycarboxamido-2-oxoazetidine-1-(α-isopropylidene)acetate.

IR$\nu_{max}^{KBr}$ cm$^{-1}$; 3280, 1738, 1710.

NMR(CDCl$_3$, ppm); 1.95(s, —CH$_3$), 2.19(s, —CH$_3$), 3.4–3.9(m, —CH$_2$—), 3.74(s, —OCH$_3$), 4.89(m, —CH—), 5.11(s, —CH$_2$—), 5.66(d, —NH—), 7.34(s, aromatic H).

REFERENCE EXAMPLE 6

To a solution of 14 g of methyl 3-benzyloxycarboxamido-2-oxoazetidine-1-(α-isopropylidene)acetate in 400 ml of dry tetrahydrofuran (=THF) are added 5.7 g of t-butyl hypochlorite and, then, a solution of 0.348 g of lithium in 32 ml methanol with stirring at −30~−20° C. The mixture is maintained at −15° C. for 30 minutes, and, after addition 1 ml of acetic acid, the solvent is distilled off. The residue is dissolved in ethyl acetate, and, after washing with water, the solvent is distilled off. The residue is chromatographed on a column of silica gel [eluted with n-hexane-ethyl acetate (1:1)] to obtain 11.1 g of methyl 3-benzyloxycarboxamido-3-methoxy-2-oxoazetidine-1-(α-isopropylidene)acetate as crystals.

m.p. 77° C.

IR$\nu_{max}^{KBr}$ cm$^{-1}$; 1761, 1723.

NMR(CDCl$_3$, ppm); 191(s, CH$_3$), 2.22(s, CH$_3$), 3.53(s, CH$_3$), 3.73(s, CH$_3$), 4.1(dd, J=6 Hz, C$_4$-H), 5.20(s, —CH$_2$—), 6.58(s, NH), 7.36(s, aromatic H).

REFERENCE EXAMPLE 7

In 3 ml of DMF is dissolved 0.313 g of 3-[D(−)-2-(4-ethyl-2,3-dioxo-1-piperazinocarboxamido)-phenylacetamido]-3-methoxy-2-oxoazetidine, followed by the addition of 0.359 g of pyridine-sulfur trioxide complex. The mixture is stirred for 5 days. To the reaction mixture is added 30 ml of diethyl ether and the oily precipitate is passed through Dowex 50 W resin (Na-form) (Dow Chemical Co., U.S.A.). The eluate is purified by Amberlite XAD-II (Rohm and Haas Co., U.S.A.) chromatography to obtain 0.202 g of sodium 3-[D(-)-2-(4-ethyl-2,3-dioxo-1-piperazinocarboxamido)-phenylacetamido]-3-methoxy-2-oxoazetidine-1-sulfonate.

IR$\nu_{max}^{KBr}$ cm$^{-1}$; 3460, 1770, 1710, 1675, 1510, 1250, 1190, 1050.

EXAMPLE 1

In 150 ml of methylene chloride is dissolved 6.0 g of methyl 3-benzyloxycarboxamido-3-methoxy-2-oxoazetidine-1-($\alpha$-isopropylidene)acetate, and ozone gas is introduced to the solution at $-50°$ C. to $-30°$ C. The reaction mixture is blue after one hour. Then, the excess ozone gas is removed by the introduction of nitrogen gas, followed by addition of dimethyl sulfide. After stirring at room temperature for an hour, the reaction mixture is washed with water and the solvent is distilled off to give 6.1 g of methyl 3-benzyloxycarboxamido-3-methoxy-2-oxoazetidine-1-$\alpha$-ketoacetate. To a solution of this product in 75 ml of methanol is added 19 ml of 0.002% sodium methoxide in methanol, and the mixture is stirred at room temperature for 15 minutes. After the addition of 0.3 g of acetic acid, the solvent is distilled off, and the residue is dissolved in ethyl acetate. The solution is washed with water, and the solvent is distilled off. The residue is chromatographed on a column of silica gel [eluted with ethyl acetate-hexane (1:1)] to obtain 2.7 g of 3-benzyloxycarboxamido-3-methoxy-2-oxoazetidine as crystals.

Optical rotation: $[\alpha]_D^{25} +68.2°$ (c=1, MeOH).
IR$\nu_{max}^{CHCl_3}$ cm$^{-1}$; 3420, 1774, 1723.
NMR(CDCl$_3$, ppm); 3.45(s, CH$_3$), 3.60(d, J=6 Hz, C$_4$-H), 3.80(d, J=6 Hz, C$_4$-H), 5.14(s, —CH$_2$—), 6.74(broad s, NH), 7.34(s, aromatic H).

EXAMPLE 2

A mixture of 2.0 g of 3-benzyloxycarboxamido-3-methoxy-2-oxoazetidine and 0.50 g of palladium black in 5 ml of THF is stirred in hydrogen gas streams for 1.5 hours. The catalyst is filtered off and the filtrate is concentrated to obtain 0.9 g of 3-amino-3-methoxy-2-oxoazetidine.

IR$\nu_{max}^{Nujol}$ cm$^{-1}$; 3250, 1740.
NMR(CDCl$_3$, ppm); 2.35(broad s, NH$_2$), 3.40(dd, J=6 Hz, C$_4$-H), 3.45(s, CH$_3$), 6.7(broad s, NH).

EXAMPLE 3

To a solution of 61 mg of 3-amino-3-methoxy-2-oxoazetidine in 2 ml of THF are added 72 mg of phenylacetic acid, 71.3 mg of 1-hydroxybenzotriazole and 130 mg of dicyclohexylcarbodiimide, and the mixture is stirred at room temperature for 3 hours. The dicyclohexylurea is filtered off, and the filtrate is concentrated. The residue is chromatographed on a column of silica gel [eluted with n-hexane-ethyl acetate (1:2)] to obtain 86 mg of 3-phenylacetamido-3-methoxy-2-oxoazetidine.

IR$\nu_{max}^{KBr}$ cm$^{-1}$; 3420, 1774, 1723.
NMR(CDCl$_3$, ppm); 3.45(s, OCH$_3$), 3.67(ABq, J=6 Hz, —CH$_2$—), 5.14(s, —CH$_2$—), 6.74(broad s, NH), 7.34(s, aromatic H).

EXAMPLE 4

In 150 ml of methylene chloride is dissolved 7.2 g of methyl 3-benzyloxycarboxamido-3-methoxy-2-oxoazetidine-1-($\alpha$-isopropylidene)acetate obtained in Reference Example 6 and ozone gas is introduced to the solution at $-50 \sim -30°$ C. The reaction mixture is blue in color after 55 minutes. Then, nitrogen gas is introduced until the solution becomes colorless. Then, 6 ml of dimethyl sulfide is added, followed by stirring at room temperature for 30 minutes. The reaction mixture is washed with water and the solvent is distilled off to give 8.1 g of methyl 3-benzyloxy-carboxamido-3-methoxy-2-oxoazetidine-1-$\alpha$-ketoacetate. This product is dissolved in 100 ml of methanol, followed by the addition of 25 ml of 0.002% sodium methoxide in methanol. The mixture is stirred at room temperature for 15 minutes, and the solvent is distilled off. The residue is dissolved in ethyl acetate and the solution is washed with water. The solvent is distilled off to give 3.3 g of 3-benzyloxycarboxamido-3-methoxy-2-oxoazetidine as crystals. In IR and NMR spectra, this product is in agreement with the optically active compound obtained in Example 1.

Optical rotation: $[\alpha]_D^{25}$ 0° (c=1, MeOH).

EXAMPLE 5

To a solution of 230 mg of 3-amino-3-methoxy-2-oxoazetidine in 3 ml of methylene chloride are added 160 mg of pyridine and, then 340 mg of carbobenzoxy chloride with stirring and under ice-cooling. After stirring at room temperature for 30 minutes, the reaction mixture is washed with water, and the solvent is distilled off. The residue is chromatographed on a column of silica gel [eluted with n-hexane-ethyl acetate (1:2)] to obtain 260 mg of 3-benzyloxycarboxamido-3-methoxy-2-oxoazetidine. In physicochemical properties, this product is in agreement with the compound obtained in Example 4.

EXAMPLE 6

A mixture of 2.2 g of 3-benzyloxycarboxamido-3-methoxy-2-oxoazetidine, 0.6 g of palladium black and 60 ml of dry THF is stirred in hydrogen gas streams for 30 minutes, after which the palladium black is filtered off. To the filtrate are added 2.4 g of D-N-carbobenzoxyalanine, a solution of 1.2 g of N-ethyl-morpholine in 5 ml dry tetrahydrofuran and 2.5 g of dicyclohexylcarbodiimide, and the mixture is stirred at room temperature for 15 hours. The dicyclohexylurea is filtered off, and the filtrate is concentrated. The residue is chromatographed on a column of silica gel (eluted with ethyl acetate) to obtain 1.46 g of 3-D-N-carbobenzoxyalaninamido-3-methoxy-2-oxoazetidine.

IR$\nu_{max}^{KBr}$ cm$^{-1}$; 3270, 1760, 1680, 1520.
NMR(CDCl$_3$, ppm); 1.41(d, J=7 Hz, —CH$_3$), 3.44(s, —OCH$_3$), 3.74(dd, J=6 Hz, —CH$_2$—), 4.38(m, —CH—), 5.11(s, —CH$_2$—), 5.70(d, J=7 Hz, —NH—), 6.78(broad s, —NH), 8.04(broad s, —NH).

EXAMPLE 7

A mixture of 0.501 g of 3-benzyloxycarboxamido-3-methoxy-2-oxoazetidine and 0.252 g of palladium black in 20 ml of THF is stirred in hydrogen gas streams for 20 minutes. The catalyst is filtered off, and the filtrate is concentrated under reduced pressure. The residue is dissolved in 20 ml of methylene chloride, and to the solution are added 10 ml of propylene oxide and a solution of the acid chloride obtained from 0.76 g of D(-)-N-(4-ethyl-2,3-dioxo-1-piperazinocarbonyl)phenylglycine in 10 ml of methylene chloride with stirring −15° C. After stirring at the same temperature for 30 minutes, 0.475 g of pyridine is added, and the mixture is further stirred for another hour. The reaction mixture is concentrated under reduced pressure and cold water is added to the residue which is then extracted with THF-ethyl acetate. The extract is washed with water and concentrated under reduced pressure. To the residue is added diethyl ether and the resultant powders are collected by filtration to obtain 0.433 g of 3-[D(-)-N-(4-ethyl-2,3-dioxo-1-piperazinocarbonyl)-phenyl-glycinamido]-3-methoxy-2-oxoazetidine.

IR$\nu_{max}^{KBr}$ cm$^{-1}$; 3270, 1760, 1710, 1670, 1505, 1190.

EXAMPLE 8

A mixture of 1.0 g of 3-benzyloxycarboxamido-3-methoxy-2-oxoazetidine and 0.6 g of palladium black in 40 ml of THF is stirred in hydrogen gas streams for 20 minutes. The catalyst is filtered off and the filtrate is concentrated under reduced pressure. The residue is dissolved in 40 ml of methylene chloride, and to the solution are added 20 ml of propylene oxide and a solution of the acid chloride prepared from 2.22 g of 2-(2-chloroacetamido-4-thiazolyl)-2-methoxyiminoacetic acid (syn-isomer) in 10 ml of methylene chloride with stirring and under cooling at −15° C. The mixture is stirred at −15° C. for 30 minutes and, after the addition of a solution of 1.58 g pyridine in 10 ml of methylene chloride, stirred for further 30 minutes. The reaction mixture is then concentrated under reduced pressure and, following addition of ice-water, the residue is extracted with THF-ethyl acetate. The extract is washed with water and concentrated under reduced pressure and the residue is purified by silica gel column chromatography. By the above procedure is obtained 0.798 g of 3-[2-(2-chloroacetamido-4-thiazolyl)-2-methoxyiminoacetamido]-3-methoxy-2-oxoazetidine.

IR$\nu_{max}^{KBr}$ cm$^{-1}$; 3280, 1760, 1675, 1540.

NMR(d$_6$-DMSO, ppm); 3.44s, —CH$_3$), 3.60(ABq, J=6, 20 Hz C$_4$-H$_2$), 3.92(s, —CH$_3$), 4.38(s, —CH$_2$—), 7.42(s, aromatic H), 8.33(s, —NH—), 9.78(s, NH), 12.75(s, —NH—).

EXAMPLE 9

In 20 ml of THF is dissolved 0.501 g of 3-benzyloxycarboxamido-3-methoxy-2-oxoazetidine (DL-form) and, after the addition of 0.3 g of palladium black, the mixture is stirred in hydrogen gas streams for 20 minutes. The catalyst is filtered off, and the filtrate is concentrated under reduced pressure. The residue is dissolved in 20 ml of methylene chloride. To the solution are added 10 ml of propylene oxide and, then, a solution of the acid chloride prepared from 0.819 g of DL-N-(4-n-octyl-2,3-dioxo-1-piperazinocarbonyl)thienylglycine in 10 ml of methylene chloride with stirring at −15° C. After stirring at the same temperature for 15 minutes, 0.391 g of pyridine is added, and the solution is stirred for further 30 minutes. The reaction mixture is poured into ice-water and extracted with chloroform. The extract is washed with water, and concentrated under reduced pressure. The residue is purified by silica gel column chromatography to obtain the following two isomers.

Isomer A: 0.437 gram of an equimolar mixture of 3-[D-2-(4-n-octyl-2,3-dioxo-1-piperazinocarboxamido)-2-thienylacetamido]-3(S)-methoxy-2-oxoazetidine and 3-[L-2-(4-n-octyl-2,3-dioxo-1-piperazinocarboxamido)-2-thienylacetamido]-3(R)-methoxy-2-oxoazetidine.

IR$\nu_{max}^{KBr}$ cm$^{-1}$; 3270, 2920, 1760, 1705, 1675.

NMR(d$_6$-DMSO, ppm); 0.86(t, CH$_3$), 3.20(s, OCH$_3$), 3.4–4.1(m, ring CH$_2$), 3.44, 3.57(ABq, J=6, 13 Hz, C$_4$-H), 5.90(d, J = 7Hz, —CH—), 6.9–7.6(m, thienyl —H), 8.36(s, NH), 9.74(d, J=7 Hz, NH).

Isomer B: 0.10 gram of an equimolar mixture of 3-[D-2-(4-n-octyl-2,3-dioxo-1-piperazinocarboxamido]-2-thienylacetamido]-3(R)-methoxy-2-oxoazetidine and 3-[L-2-(4-n-octyl-2,3-dioxo-1-piperazinocarboxamido)-2-thienylacetamido]-3(S)-methoxy-2-oxoazetidine.

IR$\nu_{max}^{KBr}$ cm$^{-1}$; 3270, 2920, 1760, 1705, 1675.

NMR(d$_6$-DMSO, ppm), 0.86(t, CH$_3$), 3.36(s, OCH$_3$), 3.39, 3.48(ABq, J=9, 6 Hz, C$_4$-H), 3.4–4.1(m, ring CH$_2$), 5,89(d, J = 7Hz, —CH—), 6.9–7.6(m, thienyl-H), 8.31(s, NH), 9.67(s, NH), 9.70(d, J=7 Hz, NH).

EXAMPLE 10

In 20 ml of THF is dissolved 0.501 g of 3-benzyloxycarboxamido-3-methoxy-2-oxoazetidine (DL-form) and with the addition of 0.3 g of palladium black, the mixture is stirred in hydrogen gas streams for 20 minutes. The catalyst is filtered off, and the filtrate is concentrated under reduced pressure. The residue is dissolved in 20 ml of methylene chloride. To the solution are added 10 ml of propylene oxide and, then, a suspension of D-α-sulfophenylacetyl chloride in 5 ml of methylene chloride under cooling at −15° C. After stirring at the same temperature for 30 minutes, 0.791 g of pyridine is added, and the mixture is stirred under ice-cooling for an hour. The reaction mixture is concentrated under reduced pressure and the residue is dissolved in an aqueous solution containing 1.01 g of sodium hydrogen carbonate. The solution is washed with ethyl acetate and the water layer is purified on an Amberlite XAD-II column to provide 0.106 g of a mixture of 3-(D-α-sulfophenylacetamido)-3(R)-methoxy-2-oxoazetidine sodium salt and 3-(D-α-sulfophenylacetamido)-3(S)-methoxy-2-oxoazetidine sodium salt.

IR$\nu_{max}^{KBr}$ cm$^{-1}$; 3270, 1745, 1670, 1200, 1040.

NMR(d$_6$-DMSO, ppm), 3.31, 3.41(s, OCH$_3$), 3.41, 3.53(ABq, J=6, 12 Hz, C$_4$-H), 5.65, 5.70(s, —CH—), 7.2–7.5(m, aromatic H), 8.29(s, NH), 9.20, 9.29(s, NH).

EXAMPLE 11

In the manner as described in Example 9, 0.500 g of 3-benzyloxycarboxamido-3-methoxy-2-oxoazetidine is treated to prepare the 3-amino compound in 20 ml of methylene chloride. To the solution is added a solution of the acid chloride prepared from 1.081 g of monobenzyl 2-phenylmalonate in 10 ml of methylene chloride and the reaction mixture is worked up in the manner as described in Example 9 to obtain 0.460 g of 3-(2-benzyloxycarbonyl-2-phenylacetamido)-3-methoxy-2-oxoazetidine.

IR$\nu_{max}^{KBr}$ cm$^{-1}$; 1775, 1722, 1685, 1493, 1160.

EXAMPLE 12

A mixture of 0.75 g of 3-benzyloxycarboxamido-3-methoxy-2-oxoazetidine, 0.4 g of palladium black and 10 ml of dry tetrahydrofuran is stirred in hydrogen gas streams for 30 minutes, and the catalyst is filtered off. The filtrate is added to a solution containing 0.97 g of 2-(4-ethyl-2,3-dioxo-1-piperazinocarboxamido)-2-(1-cyclohexen-1-yl)acetic acid, 0.35 g of N-ethylmorpholine and 10 ml of dry tetrahydrofuran, and to the mixture is added 0.64 g of dicyclohexylcarbodiimide. After stirring at room temperature, dicyclohexylurea is filtered off, and the filtrate is concentrated under reduced pressure. The residue is purified by silica gel column chromatography to obtain 0.58 g of 3-[2-(4-ethyl-2,3-dioxo-1-piperazinocarboxamido)-2-(1-cyclohexen-1-yl)acetamido]-3-methoxy-2-oxoazetidine.

IR$\nu_{max}^{KBr}$ cm$^{-1}$, 3280, 2940, 1765, 1710, 1680, 1510, 1195.

EXAMPLE 13

In 15 ml of acetonitrile is suspended 1.0 g of 2-(carbamoylamino)-2-thienylacetic acid and to the suspension is added 1.19 g of thionyl chloride under ice-cooling. The mixture is stirred for 5 minutes and concentrated under reduced pressure. The 2-amino-4-(2-thienyl)-5(4H)oxazolone hydrochloride thus obtained is suspended in 5 ml of propylene oxide. On the other hand, the 3-amino-3-methoxy-2-oxoazetidine obtained by the catalytic reduction of 0.501 g of 3-benzyloxycarboxamido-3-methoxy-2-oxoazetidine (DL-form) is dissolved in 5 ml of methylene chloride, and this solution is added to the above suspension at a temperature below $-60°$ C. The mixture is stirred at $-15°$ C. for 30 minutes and, after the addition of 2.0 g of pyridine, stirred for further 30 minutes. The reaction mixture is poured into ice-water and extracted with tetrahydrofuran-ethyl acetate. The extract is concentrated under reduced pressure, and the residue is purified by silica gel column chromatography to obtain 0.517 g of 3-[2-(carbamoylamino)-2-thienylacetamido]-3-methoxy-2-oxoazetidine.

IR$\nu_{max}^{KBr}$ cm$^{-1}$; 3440, 3340, 1760, 1650, 1525.

NMR(d$_6$-DMSO, ppm); 3.22, 3.36(s, OCH$_3$), 3.42, 3.55 (ABq, J=6, 13 Hz, C$_4$-H), 5.69(d, J = 8Hz, —CH—),
|

5.74(s, NH$_2$), 6.68, 6.72(d, J=8 Hz, NH), 6.9–7.5(m, thienyl-H), 8.28, 8.34 (s, NH), 9.45, 9.49(s, NH).

EXAMPLE 14

In 10 ml of THF is dissolved 0.500 g of 3-benzyloxycarboxamido-3-methoxy-2-oxoazetidine and, after the addition of 0.300 g of palladium black, the mixture is stirred in hydrogen gas streams for 30 minutes. The catalyst is filtered off, and the filtrate is concentrated under reduced pressure. The residue is dissolved in 20 ml of methylene chloride. To the solution are added 10 ml of propylene oxide and, then, a solution of the acid chloride prepared from 0.525 g of cyanomethylthioacetic acid in 10 ml of methylene chloride at $-15°$ C.

Then, 0.800 g of pyridine is added and the resulting mixture is stirred for an hour. After removal of the solvent under reduced pressure, water is added to the residue and the solution is extracted with THF-ethyl acetate. After washing with water, the extract is concentrated under reduced pressure to obtain 0.186 g of 3-cyanomethylthioacetamido-3-methoxy-2-oxoazetidine.

IR$\nu_{max}^{liq}$ cm$^{-1}$; 3260, 2240, 1758, 1670, 1520.

NMR(d$_6$-DMSO, ppm), 3.33(s, OMe), 3.33, 3.70(s, —CH$_2$—), 3.2–3.8(m, C$_4$-H), 8.27(s, NH), 9.28(s, NH).

EXAMPLE 15

To a solution of 1.25 g of 3-benzyloxycarboxamido-3-methoxy-2-oxoazetidine in 25 ml of THF is added 0.5 g of palladium black, the mixture is stirred in hydrogen gas streams for 30 minutes, and the catalyst is filtered off. On the other hand, to a solution of 2.23 g of D-N-carbobenzoxyalanine in 25 ml of THF are added 0.945 g of disphogene and, then, a solution of 2.02 g of triethylamine in 4 ml of THF at $-30°$ C. The mixture is then stirred at the same temperature for 30 minutes. The filtrate obtained previously is now added dropwise to this reaction mixture at $-30°$ C. and the mixture is allowed to stand at room temperature overnight. The triethylamine hydrochloride is filtered off and the filtrate is concentrated under reduced pressure. Purification of the residue by silica gel column chromatography gives 0.862 g of 3-(D-N-carbobenzoxyalanylamino)-3-methoxy-2-oxoazetidine.

IR$\nu_{max}^{KBr}$ cm$^{-1}$; 1760, 1680, 1520.

NMR(CDCl$_3$, ppm); 1.39; 1.41(each d, J=7 Hz, CH$_3$), 3.44(s, CH$_3$), 3.66, 3.70, 3.74, 3.80(each d, J=6 Hz), 4.38(m, —CH—),
|

5.11(s, CH$_2$), 5.70(d, J=7 Hz, NH), 6.45, 6.78(each s, NH), 7.90, 8.04(each s, NH).

EXAMPLE 16

A mixture of 0.482 g of 3-(D-N-carbobenzoxyalanylamino)-3-methoxy-2-oxoazetidine, 0.5 g of palladium black, 10 ml of THF and 5 ml of methanol is stirred in hydrogen gas streams for 30 minutes. The catalyst is filtered off, and the filtrate is concentrated to dryness under reduced pressure. The residue is dissolved in 2 ml of dimethylacetamide and to the solution are added 0.2 g of triethylamine and a solution of 0.337 g of 4-ethyl-2,3-dioxo-1-piperazinocarbonyl chloride in 6 ml of THF under ice-cooling and with stirring. After stirring at room temperature for an hour, the reaction mixture is filtered, and the filtrate is concentrated under reduced pressure. The residue is purified by silica gel column chromatography to provide 0.432 g of 3-[D-N-(4-ethyl-2,3-dioxo-1-piperazinocarbonyl)alanylamino]-3-methoxy-2-oxoazetidine.

IR$\nu_{max}^{KBr}$ cm$^{-1}$; 1760, 1710, 1670, 1510.

NMR(DMSO-d$_6$, ppm); 1.10(t, J=7 Hz, CH$_3$), 1.34, 1.44 (each d, J=7 Hz, —CH$_3$), 3.36(s, CH$_3$), 3.90(m, —CH$_2$—), 4.48(m, —CH—), 8.31(broad s, NH), 9.74(d, J=7 Hz, NH), 9.82(s, NH).

EXAMPLE 17

A mixture of 1 g of 3-benzyloxycarboxamido-3-methoxy-2-oxoazetidine, 0.6 g of palladium black and 20 ml of THF is stirred in hydrogen gas streams for 30 minutes, and the catalyst is filtered off.

On the other hand, to a solution of 2.28 g of D-N-carbobenzoxyphenylglycine in 20 ml of THF are added 0.8 g of diphosgene and a solution of 1.62 g of triethylamine in 4 ml of THF with stirring and under cooling at $-30°$ C. After stirring for 30 minutes, the filtrate obtained previously is now added dropwise to this reaction mixture at $-30°$ C. and the mixture is stirred at room temperature for 2 hours. The reaction mixture is filtered, and the filtrate is concentrated under reduced pressure. The residue is purified by silica gel column chromatography to provide 1.18 g of 3-(D-N-carbobenzoxyphenylglycylamino)-3-methoxy-2-oxoazetidine.

IR$\nu_{max}^{KBr}$ cm$^{-1}$; 1760, 1680, 1520.

NMR (CDCl$_3$, ppm); 3.13, 3.40(each s, CH$_3$), 3.80(m, C$_4$-H), 5.10(s, —CH$_2$—), 5.50(d, J = 7Hz, —CH—), 6.30(d, J=7 Hz, NH), 7.33 (aromatic H).

A mixture of 0.575 g of the above 3-(D-N-carbobenzoxyphenylglycylamino)-3-methoxy-2-oxoazetidine, 0.6 g of palladium black, 15 ml of THF and 5 ml of methanol is stirred in hydrogen gas streams for 2.5 hours. The catalyst is filtered off and the filtrate is concentrated to dryness.

On the other hand, to a solution of 0.571 g of D-N-carbobenzoxyphenylglycine in 8 ml of dry THF are added 0.189 g of diphosgene and a solution of 410 mg of triethylamine in 4 ml of dry THF at a temperature below $-30°$ C., and the mixture is stirred at that temperature for 30 minutes. To this mixture is added a solution of the concentrate obtained previously in 5 ml of dry THF at $-30°$ C. The mixture is allowed to stand at room temperature overnight and filtered. The filtrate is concentrated under reduced pressure and the residue is purified by silica gel column chromatography to provide 0.602 g of 3-(D-N-carbobenzoxyphenylglycyl-D-phenylglycylamino)-3-methoxy-2-oxoazetidine.

IR$\nu_{max}^{KBr}$ cm$^{-1}$; 1765, 1680, 1640, 1510.

NMR(DMSO-d$_6$+D$_2$O, ppm); 3.08, 3.26(each s, OMe), 3.40(m, CH$_4$-H), 5.06(s, —CH$_2$—), 5.45(s, —CH—), 5.59(s, —CH—), 7.2~7.55(m, aromatic H).

EXAMPLE 18

In 25 ml of THF is dissolved 2.5 g of the 3-benzyloxycarboxamido-3-methoxy-2-oxoazetidine obtained in Example 1, and to the solution is added 0.5 g of palladium black. The mixture is stirred in hydrogen gas streams for an hour, and the catalyst is filtered off.

On the other hand, a solution of 4.46 g of N-carbobenzoxy-D-alanine in 35 ml of THF is cooled to $-40°$ C. and 1.89 g of diphosgene and 4.2 g of triethylamine are added. To this solution is added the above filtrate at $-40°$ C. and the mixture is stirred at room temperature for 2 hours. The reaction mixture is filtered, the filtrate is concentrated under reduced pressure. The residue is purified by silica gel column chromatography to provide 0.905 g of 3-(N-carbobenzoxy-D-alaninamido)-3-methoxy-2-oxoazetidine.

$[\alpha]_D^{22°}$ +79.5° (c=1, MeOH).

IR$\nu_{max}^{KBr}$ cm$^{-1}$; 1755, 1680, 1515.

NMR (DMSO-d$_6$, ppm); 1.22(d, J=7 Hz, CH$_3$), 3.32 (s, CH$_3$), 3.40, 3.48(each d,J=7 Hz, C$_4$-H), 4.12(m, —CH—), 5.04(s, —CH$_2$—), 7.36(s, aromatic H), 8.26(s, NH), 8.98(d, J=7 Hz, NH).

EXAMPLE 19

In 2 ml of DMA is dissolved 0.28 g of the 3-(D-alaninamido)-3-methoxy-2-oxoazetidine obtained in Example 16, and 0.30 g of triethylamine is added. To the solution is added a solution of 0.233 g of phenylacetyl chloride in 2 ml of THF under ice-cooling and the mixture is stirred at room temperature for an hour. The mixture is concentrated under reduced pressure and the residue is extracted with ethyl acetate. The extract is purified by silica gel column chromatography to obtain 0.22 g of 3-(N-phenylacetyl-D-alaninamido)-3-methoxy-2-oxoazetidine.

IR$\nu_{max}^{KBr}$ cm$^{-1}$; 1758, 1645, 1520.

NMR(DMSO-d$_6$, ppm); 1.23, 1.24(each d, J=7 Hz, CH$_3$), 2.79, 2.95(each s, —CH$_2$—), 3.31, 3.47(each s, CH$_3$), 4.46(m, —CH—), 7.27(s, aromatic H), 8.1~8.35(m, NH), 8.98(d, J=7 Hz,NH).

EXAMPLE 20

To a solution of 0.464 g of 3-amino-3-methoxy-2-oxoazetidine in 20 ml of THF are added a solution of 1.48 g of D-2-(4-ethyl-2,3-dioxo-1-piperazinocarboxamido)-3-phenylpropionyl chloride in 15 ml of THF and a solution of 0.425 g of triethylamine in 5 ml of THF at a temperature of $-45°$ to $-30°$ C. The mixture is stirred at room temperature for 2 hours, and the precipitate is filtered off. The filtrate is concentrated. The residue is purified by silica gel column chromatography to obtain 0.865 g of 3-[D-2-(4-ethyl-2,3-dioxo-1-piperazinocarboxamido)-3-phenylpropionamido]-3-methoxy-2-oxoazetidine.

IR$\nu_{max}^{KBr}$ cm$^{-1}$, 1761, 1700, 1660, 1518, 1188.

NMR(DMSO-d$_6$, ppm); 1.09(t, J=7 Hz, CH$_3$), 3.34(s, CH$_3$), 4.72(m, —CH—), 7.29(aromatic H), 8.32(s, NH), 9.15(d, J=7 Hz, NH), 9.43(s, NH).

EXAMPLE 21

In 20 ml of THF is dissolved 0.50 g of 3-benzyloxycarboxamido-3-methoxy-2-oxoazetidine and, after the addition of 0.15 g of palladium black, the mixture is stirred in hydrogen gas streams for 30 minutes. The catalyst is filtered off and the filtrate is concentrated under reduced pressure, followed by addition of 10 ml of THF. On the other hand, to the solution of 0.952 g of 2-benzyloxycarboxamido-3-(N-methylcarbamoyl)propionic acid in 20 ml of THF are added 0.336 g of diphosgene and, then, a solution of 0.344 g of triethylamine in 2 ml of diethyl ether over a period of 15 minutes at $-30 \sim -20°$ C. After stirring at that temperature for 30 minutes, to the solution is added a solution of 0.344 g of triethylamine in 2 ml of ether over a period of 15 minutes and the mixture is stirred for an additional one hour. To this solution is added the above-prepared THF solution over a period of 15 minutes, and after an hour the mixture is stirred at room temperature for 15 hours. The insoluble matter is filtered off, and the filtrate is concentrated under reduced pressure. The residue is purified by silica gel column chromatography to provide 0.322 g of 3-[2-benzyloxycarboxamido-3-(N-methylcarbamoyl)propionamido]-3-methoxy-2-oxoazetidine.

IR$\nu_{max}^{KBr}$ cm$^{-1}$; 3360–3290, 1755, 1708, 1650.

NMR(CDCl$_3$, ppm); 2.60–3.00(m, —CH$_2$—, CH$_3$), 3.43(s, CH$_3$), 3.66(m, CH$_4$-H), 4.63(m, —CH—),
|

5.12(s, —CH$_2$—), 6.63 (broad s, NH), 6.77(broad s, NH), 7.12(s, NH), 7.33(s, aromatic H), 8.53(s,NH).

In 30 ml of ethanol is dissolved 0.322 g of 3-[2-benzyloxycarboxamido-3-(N-methylcarbamoyl)propionamido]-3-methoxy-2-oxoazetidine obtained previously, followed by addition of 0.15 g of palladium black. The mixture is stirred in hydrogen gas streams for an hour. The catalyst is filtered off and the filtrate is concentrated under reduced pressure. The residue is dissolved in 2 ml of DMA, followed by addition of 5 ml of THF. To the solution is added 0.112 g of triethylamine, followed by addition of a solution of 0.226 g of 4-ethyl-2,3-dioxo-1-piperazinocarbonyl chloride in 3 ml of THF over a period of 30 minutes at $-30°$ to $-20°$ C. The mixture is stirred under ice-cooling for 40 minutes. The insoluble matter is filtered off, the filtrate is concentrated under reduced pressure and the residue is purified by silica gel column chromatography to give 0.161 g of 3-[2-(4-ethyl-2,3-dioxo-1-piperazinocarboxamido)-3-(N-methylcarbamoyl)propionamido]-3-methoxy-2-oxoazetidine.

IR$\nu_{max}^{KBr}$ cm$^{-1}$; 3400–3270, 1762, 1705, 1668.

EXAMPLE 22

To a solution of 0.626 g of 3-benzyloxycarboxamido-3-methoxy-2-oxoazetidine in 25 ml of THF is added 0.15 g of palladium black, and the mixture is stirred in hydrogen gas streams for 30 minutes. The catalyst is filtered off and the filtrate is concentrated to about 5 ml. On the other hand, 0.911 g of 2-(4-ethyl-2,3-dioxo-1-piperazinocarboxamido)acetic acid is suspended in 25 ml of THF, followed by addition of 0.372 g of diphosgene at $-50°$ C. To this mixture is added a solution of 0.759 g of triethylamine in 3 ml of THF over a period of 10 minutes. The mixture is stirred at 0° C. for an hour, after which it is cooled to $-50°$ C. and 0.759 g of triethylamine is added. Then, the THF solution obtained previously, is added over a period of 5 minutes, the reaction temperature of the mixture is returned to room temperature over an hour. The insoluble matter is filtered off. The filtrate is concentrated under reduced pressure and the residue is purified by silica gel column chromatography to give 0.363 g of 3-[2-(4-ethyl-2,3-dioxo-1-piperazinocarboxamido)acetamido]-3-methoxy-2-oxoazetidine.

IR$\nu_{max}^{KBr}$ cm$^{-1}$; 3275, 1760, 1708, 1670.

NMR(DMSO-d$_6$, ppm); 1.18(t,J=7 Hz, CH$_3$), 3.40(s, —CH$_3$), 3.47(q,J=7 Hz, —CH$_2$—), 3.57–3.80(m, —CH$_2$—), 3.65(ABq, J=5, 11 Hz, C$_4$-H), 3.93–4.20(m, —CH$_2$—), 4.07(d, J=6 Hz, —CH$_2$—), 7.58(s, NH), 8.70(s, NH), 9.23(t, J=6 Hz, NH).

EXAMPLE 23

In 20 ml of THF is dissolved 0.501 g of 3-benzyloxycarboxamido-3-methoxy-2-oxoazetidine (DL-form) and after the addition of 0.3 g of palladium black, the mixture is stirred in hydrogen gas streams for 30 minutes. The catalyst is filtered off, the filtrate is concentrated under reduced pressure and the residue is dissolved in 20 ml of methylene chloride. To the solution are added 10 ml of propylene oxide and, then, a solution of the acid chloride prepared from 0.856 g of N-[(3-furfurylideneamino-2-oxoimidazolidin-1-yl)carboxyl]-D-phenylglycine in 10 ml of methylene chloride at $-15°$ C. The mixture is stirred at the same temperature for 15 minutes, after which 0.475 g of pyridine is added, followed by stirring for a further 30 minutes. The reaction mixture is poured into ice-water and extracted with chloroform. The extract is washed with water, dried and concentrated under reduced pressure. The residue is purified by silica gel column chromatography to obtain the following two isomers. 3-[D-2-[(3-Furfurylideneamino-2-oxoimidazolidin-1-yl)carboxamido]-2-phenylacetamido]-3(S)-methoxy-2-oxoazetidine, 0.391 g.

IR$\nu_{max}^{KBr}$ cm$^{-1}$; 3280, 1760, 1720, 1670, 1475, 1410, 1230.

NMR(d$_6$-DMSO, ppm); 3.08(s, CH$_3$), 3.42, 3.56(d,J=6 Hz, C$_4$-H), 3.79(s, —CH$_2$—), 5.62(d, J = 7Hz, —CH—),
|

6.5–7.9(m, aromatic —H), 7.73(s, —CH=N—), 8.35(s, NH), 9.04(d, J=7 Hz, NH), 9.59(s,NH). 3-[D-2-[(3-Furfurylideneamino-2-oxoimidazolidin-1-yl)carboxamido]-2-phenylacetamido]-3(R)-methoxy-2-oxoazetidiine, 0.141 g.

IR$\nu_{max}^{KBr}$ cm$^{-1}$; 3280, 1760, 1720, 1670, 1475, 1410, 1230.

NMR(d$_6$-DMSO, ppm); 3.26, 3.42(d, J=6 Hz, C$_4$-H), 3.34(s,CH$_3$), 3.78(s, —CH$_2$—), 5.61(d, J = 7Hz, —CH—),
|

6.5–7.9(m, aromatic —H), 7.73(s, —CH=N—), 8.23(s, NH), 8.98(d, J=7 Hz, NH), 9.54(s,NH).

EXAMPLE 24

In 40 ml of THF is dissolved 1 g of 3-benzyloxycarboxamido-3-methoxy-2-oxoazetidine, and after the addition of 0.2 g of palladium black, the mixture is stirred in hydrogen gas streams for 50 minutes. The catalyst is filtered off and the filtrate is concentrated to 5 ml. On the other hand, 0.92 g of 2-benzyloxycarboxamidoacetic acid is suspended in 20 ml of methylene chloride and 0.478 g of trimethylsilyl chloride is added under ice-cooling, followed by addition of a solution of 0.445 g of triethylamine in 2 ml of methylene chloride. After stirring at room temperature for an hour, the reaction mixture is cooled to $-20 \sim -15°$ C., followed by addition of 0.351 g of DMF and 0.476 g of diphosgene. The mixture is stirred at the same temperature for 2 hours. After cooling to $-60 \sim -50°$ C., to the reaction mixture is added a solution of 0.890 g of triethylamine in 3 ml of THF over a period of 10 minutes. Then, 2 ml of propylene oxide is added and the THF solution obtained previously is further added over a period of 10 minutes. The mixture is stirred at $-20 \sim -15°$ C. for 90 minutes. The insoluble matter is filtered off, the filtrate is concentrated under reduced pressure and the residue is purified by silica gel column chromatography to give 0.771 g of 3-(2-benzyloxycarboxamidoacetamido)-3-methoxy-2-oxoazetidine.

IR$\nu_{max}^{KBr}$ cm$^{-1}$; 3290, 1760, 1692, 1680

NMR(CDCl$_3$, ppm); 3.43(s, CH$_3$), 3.73(ABq, J=6, 11 Hz, C$_4$-H), 3.97(d, J=6 Hz, —CH$_2$—), 5.13(s, —CH$_2$—), 5.97(t, J=6 Hz, NH), 6.80(s, NH), 7.33(s, aromatic H), 3.10(s, NH).

EXAMPLE 25

In 20 ml of methanol is dissolved 0.454 g of 3-(2-benzyloxycarboxamidoacetamido)-3-methoxy-2-oxoazetidine, and after the addition of 0.2 g of palladium black, the mixture is stirred in hydrogen gas streams for an hour. The catalysts is filtered off and the filtrate is concentrated under reduced pressure, followed by addition of 2 ml of DMA. On the other hand, 0.497 g of 2-benzyloxycarboxamido-3-N-methylcarbamoylpropionic acid is suspended in 20 ml of methylene chloride under ice-cooling and 0.192 g of trimethylsilyl chloride is added, followed by addition of a solution of 0.179 g of triethylamine in 2 ml of methylene chloride over a period of 5 minutes. After stirring at room temperature for an hour, the reaction mixture is cooled to $-20 \sim -15°$ C., followed by addition of 0.159 g of DMF and 0.203 g of diphosgene. The mixture is stirred at the same temperature for 2 hours. After cooling to $-60 \sim -50°$ C. a solution of 0.409 g of triethylamine in 2 ml of methylene chloride is added over a period of 5 minutes. Then, after the addition of the DMA solution prepared previously and 2 ml of propylene oxide, the mixture is stirred for 20 minutes. It is further stirred at $-20 \sim -15°$ C. for 90 minutes. The insoluble matter is filtered off, the filtrate is concentrated under reduced pressure and the residue is purified by silica gel column chromatography to give 0.355 g of 3-[2-[2-benzyloxycarboxamido-3-(N-methylcarbamoyl)propionamido]acetoamido]-3-methoxy-2-oxoazetidine. IR$\nu_{max}^{KBr}$ cm$^{-1}$; 3390–3270, 1762, 1695–1650.

NMR(DMSO-d$_6$, ppm); 2.55(d, J=5 Hz, —CH$_3$), 2.40–2.60(m, —CH$_2$—), 3.30(s, —CH$_3$), 3.40(ABq, J=6, 10 Hz, C$_4$-H), 3.75(d, J=6 Hz, —CH$_2$—), 4.33(m, —CH—), 5.01(s, —CH$_2$—), 7.33(s, aromatc H), 7.70(m, NH), 8.04(d, J=5 Hz, NH), 8.25(s, NH), 8.88(s, NH), 9.10(m, NH).

EXAMPLE 26

In 20 ml of methanol is dissolved 0.566 g of 3-(2-benzyloxycarboxamidoacetamido)-3-methoxy-oxoazetidine, and after the addition of 0.3 g of palladium black, the mixture is stirred in hydrogen gas streams for an hour. The catalyst is filtered off and the residue is concentrated under reduced pressure, followed by addition of 2 ml of DMA. On the other hand, 0.898 g of 2-benzyloxycarboxamido-3-(4-ethyl-2,3-dioxo-1-piperazinocarboxamido)propionic acid is suspended in 30 ml of methylene chloride and under ice-cooling, 0.24 g of trimethylsilyl chloride is added, followed by addition of a solution of 0.224 g of triethylamine in 2 ml of methylene chloride over a period of 5 minutes. After stirring at room temperature for 40 minutes, the reaction mixture is cooled to $-20 \sim -15°$ C., followed by addition of 0.161 g of DMF and 0.218 g of diphosgene. The mixture is stirred at the same temperature for 2 hours. After cooling to $-60 \sim -50°$ C., a solution of 0.448 g of triethylamine in 2 ml of methylene chloride is added over a period of 5 minutes. Then, after the addition of the DMA solution obtained previously and 2 ml of propylene oxide, the mixture is stirred for 20 minutes. It is further stirred at $-20 \sim -15°$ C. for 90 minutes. The insoluble matter is filtered off, the filtrate is concentrated under reduced pressure ane the residue is purified by silica gel column chromatography to give 0.441 g of 3-[2-[2-benzyloxycarboxamido-3-(4-ethyl-2,3-dioxo-1-piperazinocarboxamido)propionamido]acetamido]-3-methoxy-2-oxoazetidine.

IR$\nu_{max}^{KBr}$ cm$^{-1}$; 3300, 1765, 1708, 1670.

NMR(DMSO-d$_6$, ppm); 1.08(t, J=7 Hz, —CH$_3$), 3.30(s, —CH$_3$), 3.39(q, J=7 Hz, —CH$_2$—), 3.46(ABq, J=5, 11 Hz, —CH$_2$—), 3.70-4.00 (m, —CH$_2$—), 4.20(m, —CH—), 5.03(s, —CH$_2$—), 7.33(s, aromatic —H), 7.55(d, J=9 Hz, NH), 8.12(t, J=6 Hz, NH), 8.27(s, NH), 8.90–9.17(m, NH).

EXAMPLE 27

To a solution of 0.661 g of D-4-benzyloxycarboxamido-4-benzyloxycarbonylbutyric acid in 15 ml of THF are added 0.168 g of diphosgene and 0.44 g of triethylamine under cooling at $-30°$ C. To this solution is added a solution of 0.36 g of 3-(D-phenylglycinamido)-3-methoxy-2-oxoazetidine in 5 ml of THF under cooling at $-20°$ C. and the mixture is stirred at room temperature for an hour. The reaction mixture is concentrated under reduced pressure and the residue is purified by silica gel column chromatography to obtain 0.314 g of 3-[D-2-(D-4-benzyloxycarboxamido-4-benzyloxycarbonylbutyramido)-2-phenylacetamido]-3-methoxy-2-oxoazetidine.

IR$\nu_{max}^{KBr}$ cm$^{-1}$; 1750, 1705, 1645, 1520.

NMR(DMSO-d₆, ppm); 1.90(m, —CH₂—), 2.30(m, —CH₂—), 3.09, 3.22(each s, CH₃), 4.10(m, —CH—),
|

5.04(s, —CH₂—), 5.11(s, —CH₂—), 5.58(d, J = 7Hz, —CH—),
|

7.35(s, aromatic H), 7.70(d, J=7 Hz, NH), 9.37(d, J=7 Hz, NH).

What we claim is:

1. A compound of the formula:

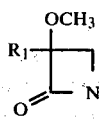

wherein R₁ is
(1) amino;
(2) amino mono-substituted by an acyl group selected from the group consisting of
(A) a group of the formula:

R₆—CO— wherein R₆ is
(i) C₁₋₆ alkyl or
(ii) a heterocyclic group selected from the group consisting of isoxazolyl, piperazinyl and imidazolinyl, said heterocyclic group being unsubstituted or mono- to tri-substituted by C₁₋₃ alkyl, C₁₋₃ alkoxy, halogen, nitro, amino, oxo, thioxo, phenyl or phenyl mono- to tri-substituted by C₁₋₃ alkyl, C₁₋₃ alkoxy, halogen, nitro or amino;
(B) a group of the formula:

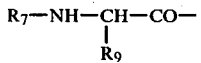

wherein R₇ is
(i) hydrogen,
(ii) an amino acid residue selected from the group consisting of glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophyl or prolyl, the said amino acid residue being unsubstituted or mono- to tri-substituted by amino, lower alkyl amino, amino-protecting group carbamoyl, methylcarbamoyl, sulfamoyl, benzyl, 4-ethyl-2,3-dioxo-1-piperazinocarbonyl or 4-ethyl-2,3-dioxo-1-piperazinocarbonylamino,
(iii) an amino-protecting group selected from the group consisting of phthaloyl, p-nitrobenzoyl, p-tert-butylbenzoyl, p-tert-butyl-benzenesulfonyl, benzenesulfonyl, toluenesulfonyl, formyl, acetyl, propionyl, monochloroacetyl, dichloroacetyl, trichloroacetyl, methanesulfonyl ethanesulfonyl, trifluoroacetyl, maloyl, succinyl, methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, diphenymethyloxycarbonyl, methoxymethyloxycarbonyl, acetylmethyloxycarbonyl, isobornyloxycarbonyl, phenyloxycarbonyl, (hexahydro-1H-azepin-1-yl)methylene, 2-amino-2-carboxyethylsulfonyl, trityl, 2-nitrophenylthio, benzylidene, 4-nitrobenzylidene, di- or trialkylsilyl, benzyl and p-nitrobenzyl, (iv) a group of the formula R₈—(CH₂)ₙ—CO— in which R₈ is
(a) a heterocyclic group selected from the group consisting of 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthyridinyl, 1,5-naphthyridinyl, 1,6-naphthyridinyl, 1,7-naphthyridinyl, 2,7-naphthyridinyl, 2,6-naphthyridinyl, quinolyl, thieno[2,3-b]pyridinyl, tetrazolyl, thiadiazolyl, oxadiazolyl, triazinyl, thienyl, pyrrolyl and furyl, said heterocyclic group being unsubstituted or mono- to tri-substituted by (1) C₁₋₁₂ alkyl, (2) C₁₋₁₂ alkyl substituted by phenyl, halogen, hydroxy or C₁₋₃ dialkylamino, (3) C₁₋₃ alkoxy, (4) hydroxy, (5) oxo, (6) thioxo, (7) formyl, (8) trifluoromethyl, (9) amino, (10) halogen, (11) n- or isopropylsulfonyl, (12) coumarin-3-carbonyl, (13) 4-formyl-1-piperazinyl, (14) pyrrolaldoimino, (15) furanaldoimino, (16) thiophenaldoimino, (17) mesyl, (18) a group selected from the group consisting of p-nitrobenzoyl, benzenesulfonyl, toluenesulfonyl, acetyl, propionyl, monochloroacetyl, dichloroacetyl, trichloroacetyl, ethanesulfonyl, trifluoroacetyl, methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, phenyloxycarbonyl, trityl, di- or trialkylsilyl, benzyl and p-nitrobenzyl, (19) C₂₋₄ alkylcarbonylamino or (20) C₂₋₄ alkylcarbonylamino mono- to tri-substituted by halogen, (b) phenyl which is unsubstituted or mono- to tri-substituted by C₁₋₃ alkyl, C₁₋₃ alkoxy, halogen, hydroxy or amino, (c) phenylthio which is unsubstituted or mono- to tri-substituted by C₁₋₃ alkyl, C₁₋₃ alkoxy, halogen, hydroxy or amino, or (d) C₁₋₃ alkylthio; n is an integer of 0 to 4; the group —(CH₂)ₙ— is unsubstituted or mono- to tri-substituted by (1) amino or (2) a group of the formula —NH—COR₈'''' wherein R₈'''' is amino, piperazinyl or piperazinyl mono- to tri-substituted by C₁₋₃ alkyl, C₁₋₃ alkoxy, hydroxy, oxo, thioxo or halogen;

(v) a group of the formula

wherein R$_8'$ and R$_8''$ are independently (a) hydrogen, (b) C$_{1-3}$ alkyl, (c) C$_{1-3}$ alkyl-carbamoyl, (d) sulfo, (e) phenylcarbonyl or (f) phenylcarbonyl mono- to tri-substituted by C$_{1-3}$ alkyl, C$_{1-3}$ alkoxy, halogen, hydroxy, sulfoxy or benzyloxy; or (vi) a group of the formula R$_8'''$—SO$_2$—
wherein R$_8'''$ is C$_{1-6}$ alkyl or C$_{1-6}$ alkyl mono- to di-substituted by amino, carboxyl, benzyloxycarbonyl or benzyloxycarbonylamino; R$_9$ is
  (i) hydrogen,
  (ii) C$_{1-3}$ alkyl which is unsubstituted or mono- to tri-substituted by phenyl, carbamoyl, methylcarbamoyl, methylthio, thienylacetamide, ethoxycarbonylmethylcarbamoyl, N-methyltetrazolylthio, halogen or sulfamoyl,
  (iii) phenyl which is unsubstituted or mono- to tri-substituted by C$_{1-3}$ alkyl, C$_{1-3}$ alkoxy, halogen, hydroxy, sulfoxy, benzyloxy, benzoyloxy, trimethylsilyl or C$_{2-10}$ alkylcarbonyloxy,
  (iv) a heterocyclic group selected from the group consisting of thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl and oxadiazolyl, said heterocyclic group being unsubstituted or mono- to tri-substituted by C$_{1-3}$ alkyl, C$_{1-3}$ alkoxy, halogen, hydroxy, nitro, sulfoxy, amino, C$_{2-4}$ alkylcarbonylamino or C$_{2-4}$ alkylcarbonylamino mono- to tri-substituted by halogen,
  (v) cyclohexenyl selected from the group consisting of cyclohexenyl and cyclohexadienyl,
  (vi) piperazinylcarbonylamino which is unsubstituted or substituted by C$_{1-12}$ alkyl, C$_{1-3}$ alkoxy, oxo, thioxo, or amino and which may have a C$_{1-3}$ alkylene chain between the piperazinyl and carbonylamino moieties;
(C) a group of the formula:

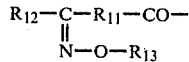

wherein R$_{11}$ is a chemical bond or a group of the formula:

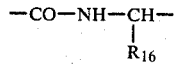

wherein R$_{16}$ is (a) C$_{1-3}$ alkyl, (b) phenyl, (c) phenyl mono- to tri-substituted by C$_{1-3}$ alkyl, C$_{1-3}$ alkoxy, halogen, nitro, amino or C$_{2-10}$ alkylcarbonyloxy, or (d) a heterocyclic group selected from the group consisting of thiazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl, the heterocyclic group being unsubstituted or mono- to tri-substituted by C$_{1-3}$ alkyl, C$_{1-3}$ alkoxy, halogen, hydroxy, amino or C$_{2-4}$ alkylcarbonylamino which is unsubstituted or mono- to tri-substituted by halogen; R$_{12}$ is (a) a heterocyclic group selected from the group consisting of 2-thiazolyl, 4-thiazolyl, 5-thiazolyl, 2-thienyl, 3-thienyl, 2-furyl, 3-furyl, 2-pyrrolyl and 3-pyrrolyl, the heterocyclic group being unsubstituted or mono- to tri-substituted by C$_{1-3}$ alkyl, C$_{1-3}$ alkoxy, hydroxy, halogen, amino or C$_{2-4}$ alkylcarbonylamino which is unsubstituted or mono- to tri-substituted by halogen, or (b) phenyl which is unsubstituted or mono- to tri-substituted by C$_{1-3}$ alkyl, C$_{1-3}$ alkoxy, halogen, nitro, amino, hydroxy, or by benzyloxy, benzoyloxy, C$_{2-10}$ alkylcarbonyloxy, γ-D-glutamyloxy or 3-amino-3-carboxypropyloxy; R$_{13}$ is (a) hydrogen, (b) C$_{2-4}$alkylcarbonyl which is unsubstituted or mono- to tri-substituted by halogen; (c) C$_{1-3}$ alkyl, or (d) a group of the formula —R$_{14}$—R$_{15}$ wherein R$_{14}$ is C$_{1-3}$ alkylene or C$_{1-3}$ alkenylene, and R$_{15}$ is carboxyl, methyl ester of carboxyl, ethyl ester of carboxyl, propyl ester of carboxyl or morpholino;

(D) a group of the formula:

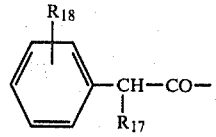

wherein R$_{17}$ is (a) hydroxy, (b) sulfoxy, (c) carboxyl, (d) sulfamoyl, (e) sulfamoyl mono- to tri-substituted by C$_{1-3}$ alkyl or amidino, (f) sulfo, (g) phenoxy carbonyl, (h) phenoxy carbonyl mono- to tri-substituted by C$_{1-3}$ alkyl or C$_{1-3}$ alkoxy, (i) benzyloxycarbonyl or (j) formyloxy; R$_{18}$ is (a) hydrogen, (b) C$_{1-3}$ alkyl, (c) C$_{1-3}$ alkoxy, (d) halogen, (e) nitro or (f) hydroxy; and (E) a group of the formula:

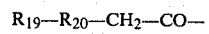

wherein R$_{19}$ is (a) cyano, (b) phenyl, (c) phenyl mono- to tri-substituted by C$_{1-3}$ alkyl, C$_{1-3}$ alkoxy, halogen, nitro, amino, hydroxy, aminomethyl or aminomethyl mono- to tri-substituted by carbamoyl, (2-oxo-3-benzylideneaminoimidazolidin-1-yl)carbonyl or (2-oxoimidazolidin-1-yl)carbonyl, (d) phenoxy, (e) phenoxy mono- to tri-substituted by C$_{1-3}$ alkyl, C$_{1-3}$ alkoxy, halogen, nitro, amino, hydroxy, or aminomethyl, (f) C$_{1-6}$ alkyl in the case where R$_{20}$ is —S—, (g) C$_{1-6}$ alkyl mono- to tri-substituted by halogen, hydroxy, cyano or trifluoromethyl, (h) alkenyl selected from the group consisting of vinyl and propenyl, said alkenyl being unsubstituted or mono- to tri-substituted by carboxyl or cyano; or (i) a heterocyclic group selected from the group consisting of 2-thienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiinyl, said heterocyclic group being unsubstituted or mono- to tri-substituted by C$_{1-3}$ alkyl, C$_{1-3}$ alkoxy, halogen, nitro, hydroxy, amino, carboxyl, oxo, C$_{2-4}$ alkylcarbonylamino, C$_{2-4}$ alkylcarbonylamino mono- to tri-substituted by halogen or C$_{2-4}$ alkylcarbonyl; R$_{20}$ is a chemical bond or —S—; or (3) amino protected by an amino-protecting group selected from the group consisting of phthaloyl, p-nitrobenzoyl, p-tert-butylbenzoyl, p-tert-butylbenzenesulfonyl, benzenesulfonyl, toluenesulfonyl, formyl, monochloroacetyl, dichloroacetyl, trichloroacetyl, methanesulfonyl, ethanesulfonyl, trifluoroacetyl, maloyl, succinyl, methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl, (hexahydro-1H-azepin-1-yl)methylene, 2-amino-2-carboxyethylsulfonyl, trityl, 2-nitrophenylthio, benzylidene, 4-nitrobenzylidene, di- or trialkylsilyl, benzyl and p-nitrobenzyl.

2. A compound as claimed in claim 1, wherein $R_1$ is amino mono-substituted by an acyl group of the formula:

$$R_6-CO-$$

wherein $R_6$ is (i) $C_{1-6}$ alkyl, or (ii) a heterocyclic group selected from the group consisting of isoxazolyl, piperazinyl and imidazolinyl, said heterocyclic group being unsubstituted or mono- to tri-substituted by $C_{1-3}$ alkyl, halogen, oxo, phenyl or phenyl mono- to tri-substituted by $C_{1-3}$ alkyl or halogen.

3. A compound as claimed in claim 1, wherein $R_1$ is amino mono-substituted by a group of the formula:

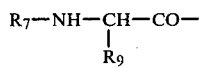

wherein $R_7$ is
(i) hydrogen,
(ii) an amino acid residue selected from the group consisting of glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophyl or prolyl, the said amino acid residue being unsubstituted or mono- to tri-substituted by amino, amino-protecting group, carbamoyl, sulfamoyl or 4-ethyl-2,3-dioxo-1-piperadinocarbonyl,
(iii) an amino-protecting group selected from the group consisting of phthaloyl, formyl, monochloroacetyl, dichloroacetyl, trichloroacetyl, ethanesulfonyl, trifluoroacetyl, maloyl, succinyl, methoxycarbonyl, t-butoxycarbonyl, β,β,β-trichloroethoxycarbonyl, benzyloxycarbonyl, p-nitrobenzyloxycarbonyl, p-nitrobenzyloxycarbonyl trityl, 2-nitrophenylthio, benzylidene, 4-nitrobenzylidene, di- or trialkylsilyl, benzyl and p-nitrobenzyl,
(iv) a group of the formula $R_8-(CH_2)_n-CO-$ in which $R_8$ is (a) a heterocyclic group selected from the group consisting of 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, osoxazolyl, pyrido[2,3-d]pyridimidinyl, benzopyranyl, 1,8-naphthyridinyl, 1,5-naphthyridinyl, 1,6-naphthyridinyl, 1,7-naphthyridinyl, 2,7-naphthyridinyl, 2,6-naphthyridinyl, guinolyl, thieno[2,3-b]pyridinyl, tetrazolyl, thiadiazolyl, oxadiazolyl, triazinyl, thienyl, pyrrolyl and furyl, said heterocyclic group being unsubstituted or mono- to tri-substituted by (1) $C_{1-12}$ alkyl, (2) $C_{1-12}$ alkyl mono- to tri-substituted by phenyl, halogen, hydroxy or $C_{1-3}$ dialkylamino, (3) hydroxy, (4) oxo, (5) thioxo, (6) amino, (7) halogen, (8) furanaldoimino, (9) thiophenaldoimino, (10) a group selected from the group consisting of p-nitrobenzoyl, benzenesulfonyl, toluenesulfonyl, acetyl, propionyl, monochloroacetyl, dichloroacetyl, trichloroacetyl, ethanesulfonyl, trifluoroacetyl, methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, phenyloxycarbonyl, trityl, di- or trialkylsilyl, benzyl and p-nitrobenzyl, (11) $C_{2-4}$ alkylcarbonylamino or (12) $C_{2-4}$ alkylcarbonylamino mono- to tri-substituted by halogen; (b) phenyl which is unsubstituted or mono- to tri-substituted by $C_{1-3}$ alkoxy, halogen or hydroxy; (c) phenylthio which is unsubstituted or mono- to tri-substituted by $C_{1-3}$ alkoxy or halogen; or (d) $C_{1-3}$ alkylthio;
n is an integer of 0 to 4; the group $-(CH_2)_n-$ is unsubstituted or mono- to tri-substituted by (1) amino or (2) a group of the formula $-NH-COR_8''''$ wherein $R_8''''$ is amino, piperazinyl or piperazinyl mono- to tri-substituted by $C_{1-3}$ alkyl, $C_{1-3}$ alkoxy, hydroxy, oxo, thioxo or halogen,
(v) a group of the formula

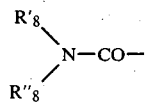

wherein $R_8'$ and $R_8''$ are independently (a) hydrogen, (b) $C_{1-3}$ alkyl, (c) $C_{1-3}$ alkylcarbamoyl, (d) sulfo, (e) phenylcarbonyl or (f) phenylcarbonyl mono- to tri-substituted by $C_{1-3}$ alkoxy or halogen; or
(vi) a group of the formula $R_8'''-SO_2-$ wherein $R_8'''$ is $C_{1-6}$ alkyl or $C_{1-16}$ alkyl mono- to di-substituted by amino carboxyl, benzyloxycarbonyl or benzyloxycarbonylamino;
$R_9$ is
(i) hydrogen,
(ii) $C_{1-3}$ alkyl which is unsubstituted or mono- to tri-substituted by carbamoyl, halogen, or sulfamoyl;
(iii) phenyl which is unsubstituted or mono- to tri-subsituted by $C_{1-3}$ alkoxy, halogen or hydroxy;
(iv) a heterocyclic group selected from the group consisting of thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl and oxadiazolyl, said heterocyclic group being unsubstituted or mono- to tri-substituted by amino, $C_{2-4}$ alkylcarbonylamino or $C_{2-4}$ alkylcarbonylamino mono- to tri-substituted by halogen; (v) cyclohexenyl selected from the group consisting of cyclohexenyl and cyclohexadienyl, or (vi) piperazinylcarbonylamino which is unsubstituted or mono- or tri-substituted by $C_{1-12}$ alkyl, oxo or thioxo and which may have a $C_{1-3}$ alkylene chain between the piperazinyl and carbonylamino moieties.

4. A compound as claimed in claim 1, wherein $R_1$ is amino mono-substituted by a group of the formula:

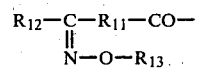

wherein $R_{11}$ is a chemical bond or a group of the formula

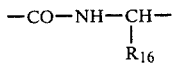

wherein $R_{16}$ is (a) $C_{1-3}$ alkyl, (b) phenyl, (c) phenyl mono- to tri-substituted by $C_{1-3}$ alkoxy or halogen, or (d) a heterocyclic group selected from the group consisting of triazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl, said heterocyclic group being unsubstituted or mono- to tri-substituted by halogen, amino, $C_{2-4}$ alkylcarbonylamino or $C_{2-4}$ alkylcarbonylamino mono- to tri-substituted by halogen, $R_{12}$ is (a) a heterocyclic group selected from the group consisting of 2-thiazolyl, 4-thiazolyl, 5-thiazolyl, 2-thienyl, 3-thienyl, 2-furyl, 3-furyl, 2-pyrrolyl and 3-pyrrolyl, said heterocyclic group being unsubstituted or mono- to tri-substituted by hydroxy, halogen, amino, $C_{2-4}$ alkylcarbonylamino or $C_{2-4}$ alkylcarbonylamino mono- to tri-substituted by halogen, or (b) phenyl which is unsubstituted or mono- to tri-substituted by $C_{1-3}$ alkoxy, halogen, hydroxy or benzyloxy, $R_{13}$ is (a) hydrogen, (b) $C_{2-4}$ alkylcarbonyl, (c) $C_{2-4}$ alkylcarbonyl mono- to tri-substituted by halogen, (d) $C_{1-3}$ alkyl, or (e) a group of the formula $-R_{14}-R_{15}$ wherein $R_{14}$ is $C_{1-3}$ alkylene or $C_{1-3}$ alkenylene and $R_{15}$ is carboxyl, methyl ester of carboxyl or morpholino.

5. A compound as claimed in claim 1, wherein $R_1$ is amino mono-substituted by a group of the formula:

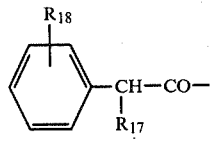

wherein $R_{17}$ is (a) hydroxy, (b) sulfoxy, (c) carboxyl, (d) sulfamoyl, (e) sulfo, (f) phenoxy carbonyl, (g) phenoxy carbonyl substituted by $C_{1-3}$ alkoxy, (h) benzyloxycarbonyl or (i) formyloxy, and $R_{18}$ is (a) hydrogen, (b) $C_{1-3}$ alkyl, (c) $C_{1-3}$ alkoxy, (d) halogen, (e) nitro or (f) hydroxy.

6. A compound as claimed in claim 1, wherein $R_1$ is amino mono-substituted by a group of the formula $$R_{19}-R_{20}-CH_2-CO-$$

wherein $R_{19}$ is (a) cyano, (b) phenyl, (c) phenyl mono- to tri-substituted by $C_{1-3}$ alkoxy, halogen, amino, hydroxy or aminomethyl, (d) phenoxy, (e) phenoxy mono- to tri-substituted by $C_{1-3}$ alkoxy, halogen, or hydroxy, (f) $C_{1-6}$ alkyl in the case where $R_{20}$ is —S—, (g) $C_{1-6}$ alkyl mono- to tri-substituted by halogen or cyano, (h) alkenyl selected from the group consisting of vinyl and propenyl, said alkenyl being unsubstituted or mono- to tri-substituted by carboxyl or cyano, or (i) a heterocyclic group selected from the group consisting of 2-thienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiinyl; and $R_{20}$ is a chemical bond or —S—.

7. A compound as claimed in claim 1, wherein $R_1$ is amino mono-protected by an amino-protecting group selected from the group consisting of phthaloyl, formyl, monochloroacetyl, dichloroacetyl, trichloroacetyl, methoxycarbonyl, t-butoxycarbonyl, $\beta,\beta,\beta$-trichloroethoxycarbonyl, benzyloxycarbonyl, p-nitrobenzyloxycarbonyl, p-methoxybenzyloxycarbonyl, trityl, dialkylsilyl and trialkylsilyl.

8. A compound as claimed in claim 1, wherein the compound is 3-amino-3-methoxy-2-oxoazetidine.

9. A compound as claimed in claim 1, wherein the compound is 3-benzyloxycarboxamido-3-methoxy-2-oxoazetidine.

10. A compound as claimed in claim 1, wherein the compound is 3-phenylacetamido-3-methoxy-2-oxoazetidine.

11. A compound as claimed in claim 1, wherein the compound is 3-[D-(-)-N-(4-ethyl-2,3-dioxo-1-piperazinocarbonyl)phenylglycinamido]-3-methoxy-2-oxazetidine.

12. A compound as claimed in claim 1, wherein the compound is 3-[D-2-(4-n-octyl-2,3-dioxo-1-piperazinocarboxamido)-2-thienylacetamido]-3(R)-methoxy-2-oxoazetidine.

* * * * *

UNITED STATES PATENT AND TRADEMARK OFFICE
CERTIFICATE OF CORRECTION

PATENT NO. : 4,416,817

DATED : November 22, 1983

INVENTOR(S) : TAISUKE MATSUO and MICHIHIKO OCHIAI

It is certified that error appears in the above—identified patent and that said Letters Patent is hereby corrected as shown below:

In section "[57] ABSTRACT", change the first formula to read as follows:

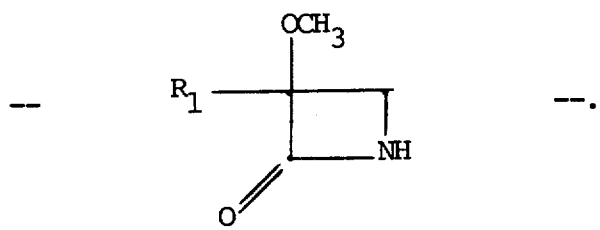

In column 3, line 16, change "γ-glutamykl" to -- γ-glutamyl--;

line 22, change "piperadinocarbonyl" to read --piperazinocarbonyl--;

line 23, change "piperidinocarbonylamino" to read --piperazinocarbonylamino--.

In column 6, line 1, change "oxadiaxolyl" to --oxadiazolyl--.

In column 10, line 14, change "methoxyiminoacetamido[acetyl" to read --methoxyiminoacetamidoacetyl--.

UNITED STATES PATENT AND TRADEMARK OFFICE
CERTIFICATE OF CORRECTION

PATENT NO. : 4,416,817

DATED : November 22, 1983

INVENTOR(S) : TAISUKE MATSUO and MICHIHIKO OCHIAI

It is certified that error appears in the above—identified patent and that said Letters Patent is hereby corrected as shown below:

In column 11, line 50, change the left hand portion of the formula to read as follows:

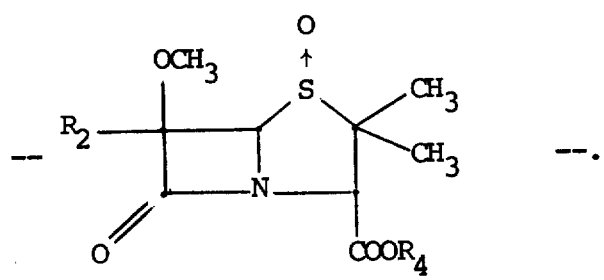

Column 15, line 54, change "he" to --the--.

Column 25, line 39, change "3.44s, -$CH_3$)" to read --3.44(s,-$CH_3$)--.

Column 34, line 12, change "methoxy-oxoazeti-" to read --methoxy-2-oxoazeti- --.

UNITED STATES PATENT AND TRADEMARK OFFICE
CERTIFICATE OF CORRECTION

PATENT NO. : 4,416,817
DATED : November 22, 1983
INVENTOR(S) : TAISUKE MATSUO and MICHIHIKO OCHIAI It is certified that error appears in the above—identified patent and that said Letters Patent is hereby corrected as shown below:

In column 35, line 20, change the formula to read:

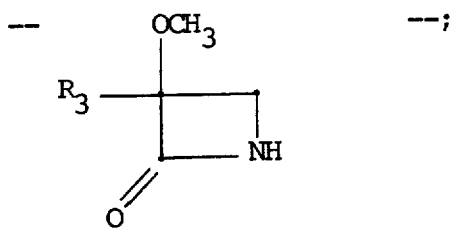

line 58, change "group carbamoyl" to --group, carbamoyl--.

In column 39, line 36, change "piperadinocarbonyl" to --piperazinocarbonyl--;

line 44, change "nyl trityl" to --nyl, trityl--;

line 52, change "osoxazolyl" to --isoxazolyl--;

line 53, change "d]pyridimidinyl" to --d]pyrimidinyl--;

line 56, change "guinolyl" to --quinolyl--.

UNITED STATES PATENT AND TRADEMARK OFFICE
CERTIFICATE OF CORRECTION

PATENT NO. : 4,416,817

DATED : November 22, 1983

INVENTOR(S) : TATSUKE MATSUO and MICHIHIKO OCHIAI

It is certified that error appears in the above—identified patent and that said Letters Patent is hereby corrected as shown below:

In column 41, line 9, change "triazolyl" to --thiazolyl--.

Signed and Sealed this

Fifth Day of June 1984

[SEAL]

Attest:

GERALD J. MOSSINGHOFF

Attesting Officer

Commissioner of Patents and Trademarks